US012740699B2

(12) United States Patent
Kucur et al.

(10) Patent No.: US 12,740,699 B2
(45) Date of Patent: Sep. 22, 2026

(54) METHOD FOR OBTAINING A VISUAL FIELD MAP OF AN OBSERVER

(71) Applicant: UNIVERSITÄT BERN, Bern (CH)

(72) Inventors: Serife Seda Kucur, Renens (CH); Raphael Sznitman, Lausanne (CH)

(73) Assignee: UNIVERSITÄT BERN, Bern (CH)

( * ) Notice: Subject to any disclaimer, the term of this patent is extended or adjusted under 35 U.S.C. 154(b) by 620 days.

(21) Appl. No.: 18/046,522

(22) Filed: Oct. 14, 2022

(65) Prior Publication Data

US 2023/0087264 A1 Mar. 23, 2023

Related U.S. Application Data

(63) Continuation-in-part of application No. 16/647,889, filed as application No. PCT/EP2018/075251 on Sep. 18, 2018, now Pat. No. 11,471,040.

(30) Foreign Application Priority Data

Sep. 18, 2017 (EP) .................................... 17191557

(51) Int. Cl.
*A61B 3/024* (2006.01)

(52) U.S. Cl.
CPC .................................... *A61B 3/024* (2013.01)

(58) Field of Classification Search
CPC ...................................................... A61B 3/024
USPC ......................................................... 351/246
See application file for complete search history.

(56) References Cited

U.S. PATENT DOCUMENTS 3,883,235 A * 5/1975 Lynn ...................... A61B 3/024 351/224
4,822,162 A * 4/1989 Richardson ............ A61B 5/398 351/243
5,864,385 A * 1/1999 Gonzales de la Rosa ................. A61B 3/024 351/224
2008/0278682 A1* 11/2008 Huxlin ..................... A61H 5/00 351/203
2009/0091706 A1* 4/2009 Derr ........................ A61B 3/10 351/205
2010/0249532 A1* 9/2010 Maddess ................ A61B 3/024 600/300

(Continued)

FOREIGN PATENT DOCUMENTS

EP 2361547 8/2011
WO 0040140 7/2000
WO 2015027225 2/2015

*Primary Examiner* — Sharrief I Broome
(74) *Attorney, Agent, or Firm* — JMB Davis Ben-David

(57) ABSTRACT

Described herein is a method for obtaining a visual field map of an observer, particularly a perimetry method, wherein a plurality of test locations in front of the observer is provided, at each test location of a subset of said plurality a respective perceived sensitivity threshold is measured, wherein at least one light signal is provided at the respective test location, and wherein it is monitored whether said observer observes said at least one light signal, and wherein for each test location a respective estimate of the perceived sensitivity threshold is derived from the previously measured perceived sensitivity thresholds of said subset, and wherein said light signal is provided at a light intensity value derived from the estimate of the perceived sensitivity threshold of said respective test location.

16 Claims, 13 Drawing Sheets

(56) References Cited

U.S. PATENT DOCUMENTS

| | | | | |
|---|---|---|---|---|
| 2010/0280405 | A1* | 11/2010 | Musialik | A61B 3/0091 600/558 |
| 2018/0192907 | A1* | 7/2018 | Siwoff | A61B 5/291 |

* cited by examiner

RMSE
10.0
7.5
5.0
2.5
ZEST
DTS
SORS-D (36)
SORS-Z (36)
SORS-D (16)
SORS-Z (16)
TOP
SEP
Number of Presentations
200
150
100
50

ZEST
Mean: -0.85
SD: 3.7
N = 134190
DTS
Mean: -0.55
SD: 3.7
N = 134190
TOP
Mean: 0.34
SD: 5.7
N = 134190
SORS-D
Mean: 0.12
SD: 3.7
N = 134190
SORS-D: Tested locations
Mean: 0.15
SD: 3.3
N = 89460
SORS-D: Untested locations
Mean: 0.05
SD: 4.4
N = 44730
SORS-Z
Mean: -0.72
SD: 3.8
N = 134190
SORS-Z: Tested locations
Mean: -0.68
SD: 3.4
N = 89460
SORS-Z: Untested locations
Mean: -0.79
SD: 4.5
N = 44730
1.00
0.75
0.50
0.25
0.00
-20
0
20
40
Normalized counts of locations
True PST - Estimated PST ZEST
Median= 2.49
SORS-Z
Median= 1.95
DTS
Median= 2.35
SORS-D
Median= 1.95
Number of locations
5000
4000
3000
2000
1000
0
0
5
10
15
SD of retests per location RMSE
6
5
4
3
2
ZEST
DTS
SORS-D (36)
SORS-Z (36)
SORS-D (16)
SORS-Z (16)
TOP
Number of Presentations
200
150
100
50
ZEST
DTS
SORS-D (36)
SORS-Z (36)
SORS-D (16)
SORS-Z (16)
TOP
RMSE
10.0
7.5
5.0
2.5
ZEST
DTS
SORS-D (36)
SORS-Z (36)
SORS-D (16)
SORS-Z (16)
TOP
Number of Presentations
200
150
100
50
ZEST
DTS
SORS-D (36)
SORS-Z (36)
SORS-D (16)
SORS-Z (16)
TOP Median RMSE
Median number of presentations
Median number of stimuli presentations
1
2
3
4
5
6
7
8
9
10

METHOD FOR OBTAINING A VISUAL FIELD MAP OF AN OBSERVER

CROSS-REFERENCE TO RELATED APPLICATIONS

This is a continuation in part of U.S. patent application Ser. No. 16/647,889 filed on Mar. 17, 2020, which is the U.S. National Stage of International Patent Application No. PCT/EP2018/075251 filed on Sep. 18, 2018, which in turn claims the benefit of European Patent Application No. 17191557.2 filed on Sep. 18, 2017. The contents of the foregoing patent applications are incorporated by reference herein in their entirety.

FIELD

The invention relates to a method for obtaining a visual field map of an observer, particularly by means of a perimetry method, such as Standard Automated Perimetry.

BACKGROUND

Standard Automated Perimetry (SAP) is one of the most commonly used techniques for measuring a subject's (or observer's) perceived visual ability. For a given eye, it provides quantitative measurements of visual function represented as a two-dimensional spatial visual field map (also termed visual field, see FIG. 1). As a medical imaging system, it is of great clinical importance for diagnosing and monitoring numerous ophthalmic diseases (e. g., glaucoma) and for detecting neurological conditions.

The goal of Standard Automated Perimetry is to determine at each location of the visual field the perceived sensitivity threshold (PST), i. e., the brightness level with which a subject observes a stimulus 50% of the time (in other words at 50% probability). Using a perimeter machine, this is achieved using a semi-automated query-response procedure: while fixating their gaze at a central point on a screen, a subject (also termed observer) is presented with light stimuli (also termed light signals) of adaptively selected brightness at different locations of the visual field and is asked to press a button whenever the stimulus is perceived. As such, the responses of subjects are inherently noisy and response reliability reduces overtime due to fatigue effects.

While presenting all brightness levels at all locations multiple times would provide many responses and allow one to average out response noise, doing so would be extremely time consuming (i. e., more than 15 minutes per eye) further worsening the induced fatigue-bias. Conversely, testing one stimulus at a handful of locations would produce highly inaccurate visual fields and be ill-suited for clinical use. As such, a central goal of Standard Automated Perimetry testing strategies is to optimize which locations to test and how often they should be tested in order to be both fast and accurate.

A number of Standard Automated Perimetry strategies have been introduced in the literature and are now common in manufactured devices. They commonly rely on staircasing schemes as in the Dynamic Test Strategy (DTS) and in Tendency Oriented Perimetry (TOP) where the intensity of presented stimuli changes by fixed or adaptive step sizes according to the patient responses. Alternative methods have also been introduced such as the Zippy Estimation by Sequential Testing (ZEST), where the next stimulus is determined by leveraging patient responses within a Bayesian model. While these methods are commonly used in clinics, none of them are simultaneously fast and accurate enough.

Some recent developments focused on spatial models where the neighboring information is exploited in a customized or data-driven manner. These approaches have been shown to lead to similar or better accuracy than ZEST. However, they typically keep the test time either the same or only bring speed improvements in healthy subjects. A more recent attempt to improve speed-accuracy trade-off has been presented where a graphical model of the visual field was presented and allows response information to propagate during an examination leading to shorter test time. This strategy however is sensitive to the selection of model parameters and therefore relies on an optimization procedure.

SUMMARY AND DETAILED DESCRIPTION

Therefore, the objective of the present invention is to provide a method for obtaining a visual field map of an observer which is improved in respect of the above-stated disadvantages of the prior art. In particular, the objective of the present invention is to provide a fast and accurate method for obtaining a visual field map of an observer.

This objective is attained by the subject matter of claim 1. Dependent claims 2 to 15 relate to embodiments of the method which are described hereafter.

The invention relates to a method for obtaining a visual field map of an observer, wherein

- a plurality of test locations in front of the observer is provided,
- at each test location of a subset of the plurality of test locations a respective perceived sensitivity threshold of the observer is measured, wherein at least one light signal is provided at the respective test location of the subset, and wherein it is monitored whether the observer observes the at least one light signal, and wherein
- for each test location of the plurality of test locations a respective estimate of the perceived sensitivity threshold is derived from the previously measured perceived sensitivity thresholds, particularly all previously measured perceived sensitivity thresholds, of the subset of test locations, and wherein
- in case at least one perceived sensitivity threshold of the test locations of the subset has been measured, the at least one light signal at a respective test location of the subset is provided at a light intensity value which is derived from the previously derived estimate of the perceived sensitivity threshold of the respective test location, and wherein
- the visual field map of the observer is obtained from the estimates of the perceived sensitivity threshold of the plurality of test locations, in particular after measuring the perceived sensitivity thresholds at all test locations of the subset.

Therein, the visual field map is a two-dimensional array of perceived sensitivity thresholds (or estimates thereof) of a given observer, wherein each perceived sensitivity threshold is allocated to a respective test location. In particular, during perimetry testing, the test locations are arranged in a plane which is perpendicular to a line of sight of the observer. When the light signals are presented to the observer, the observer's gaze is particularly fixed at a selected point, such that the respective test location, at which the light signal is presented, is positioned at a specific angle with respect to the line of sight and therefore reflects a specific point of the observer's visual field. In particular, the visual field map is separately obtained for each eye of the observer.

In the scope of the present specification, the perceived sensitivity threshold is defined by the light intensity value of the respective light signal at which the observer has a 50% probability of observing the light signal. In particular, the perceived sensitivity threshold reflects a light sensitivity of the observer at the respective test location. For example, the perceived sensitivity threshold can be measured using a db scale. According to the method of the invention, the perceived sensitivity threshold at an individual test location can be measured by many different methods, in particular those known from the prior art, such as the Dynamic Test Strategy or ZEST.

The method according to the invention comprises measuring the perceived sensitivity threshold at a subset of the plurality of test location. Therein, the subset may comprise any number of test locations from one to the total number of test locations. In other words, the perceived sensitivity threshold can be particularly measured at only some of the test locations (wherein the perceived sensitivity threshold of the remaining test locations is estimated) or at all test locations. Measuring the perceived sensitivity threshold at only some of the test locations advantageously increases the speed of the method.

Monitoring whether the observer observes the light signal may comprise detecting a feedback of the observer when the observer has observed the respective light signal. For example, the observer may provide such a feedback by pressing a button or similar means or by verbal indication to an examiner.

For each test location of the plurality of test locations a respective estimate of the perceived sensitivity threshold is derived from the previously measured perceived sensitivity thresholds, of the subset of test locations. In other words, the estimate of the perceived sensitivity threshold for a respective test location is not only derived from previous measurements of the same test location, but also from previous measurements of other test locations.

In case at least one perceived sensitivity threshold of the test locations of the subset has been measured, the light intensity value of the at least one light signal is derived from the previously derived estimate of the perceived sensitivity threshold of the respective test location. Therein, in particular, the light intensity value of a given light signal may be equal to the previously estimated perceived sensitivity threshold. In other words, the light signal may be presented at the currently estimated threshold value. In case of the first measurement, that is if no perceived sensitivity threshold has been previously measured, the light intensity of the light signal can be arbitrarily chosen or determined according to other means, such as for example an initial estimate or a population average of the perceived sensitivity threshold at the given test location.

In particular, the described method (which is also termed Sequentially Optimized Reconstruction Strategy, SORS) represents a meta-strategy which is capable of using traditional staircase methods or ZEST-like Bayesian strategies at individual locations but in a more efficient and faster manner. Therein, in particular, it can be determined which locations should be chosen and in what order they should be evaluated in order to maximally improve the estimates of the perceived sensitivity thresholds in the least amount of time. This brings a large improvement when compared to existing methods of the prior art in terms of speed, while suffers less from estimate errors.

In particular, the method comprises sequentially determining locations that most effectively reduce visual field estimation errors in an initial training phase, wherein perceived sensitivity thresholds are measured at these test locations at examination time. This approach can be easily combined with existing perceived sensitivity threshold estimation schemes to speed up the examinations. Compared to state-of-the-art strategies, this approach shows marked performance gains with a better accuracy-speed trade-off regime for both mixed and sub-populations.

In particular, in the method according to the invention, visual fields are reconstructed from a limited number of measurements by means of correlations between visual field locations, wherein during an initial training phase, the method sequentially estimates the order in which different locations should be tested to reconstruct visual fields most accurately.

In certain embodiments, the method comprises a plurality of measurement steps, wherein in each measurement step a respective perceived sensitivity threshold of the observer at a respective test location of the subset is measured, wherein at least one light signal is provided at the respective test location of the subset, and wherein it is monitored whether the observer observes the at least one light signal.

In certain embodiments, the method comprises a plurality of estimation steps, wherein in each estimation step a respective estimate of the perceived sensitivity threshold at a respective test location is derived from the previously measured perceived sensitivity thresholds, particularly all previously measured perceived sensitivity thresholds, of the subset of test locations, and wherein each estimation step is performed subsequently to a respective measurement step.

In certain embodiments, the number of test locations in the subset is smaller than the number of test locations in the plurality of test locations. This has the advantage of increased speed.

In certain embodiments, the respective estimate of the perceived sensitivity threshold is derived from the previously measured perceived sensitivity thresholds of the subset of test locations by means of a mathematical function, particularly a deterministic function, defining a relationship between the respective estimate and the previously measured perceived sensitivity thresholds.

In certain embodiments, the function is a linear function. Alternatively, the function may be a non-linear function.

The correlations between the perceived sensitivity thresholds of different test locations can be mathematically described as functions, particularly linear functions, which advantageously allows a fast estimation of the perceived sensitivity threshold at non-measured test locations.

In certain embodiments, a sequence $\Omega_S$ comprising the test locations of the subset is provided, wherein the respective perceived sensitivity thresholds of the test locations of the subset are measured in the order of the sequence $\Omega_S$. In other words, the order of test locations, at which the perceived sensitivity threshold of the observer is obtained, is determined by the sequence.

In particular, the sequence is a pre-determined sequence, in other words the sequence is provided before measuring the first perceived sensitivity threshold. Alternatively, the sequence may be provided by determining a subsequent test location after a respective perceived sensitivity has been measured at a respective test location. Therein, in particular, the subsequent test location of the sequence is derived from the at least one previously measured perceived sensitivity threshold and/or from the previously derived sensitivity estimates.

In the method of the present invention, the perceived sensitivity threshold is particularly not measured at all test locations, and it has been found that the order of test locations at which measurements are performed influences the speed of the method as well as the accuracy of the estimates.

In certain embodiments, a set of reconstruction matrices D including $$D_k^{I_k^*}$$

matrices wherein k={1, 2, . . . , S} matrices composed of k columns and M rows is provided, wherein M designates the number of test locations in the plurality of test locations, and wherein S designates the number of test locations in the subset of test locations, and wherein S≤M, wherein the reconstruction matrix $$D_k^{I_k^*}$$

comprising coefficients of said linear function, wherein each coefficient is a respective element of the reconstruction matrix, and wherein a respective vector $\hat{e}_k$ of estimates of the perceived sensitivity threshold is derived from the previously measured perceived sensitivity thresholds of the subset of test locations by means of the formula $$\hat{e}_k = D_k^{I_k^*} y_{\Omega_k^*},$$

wherein k={1, 2, . . . , S}, and wherein $$y_{\Omega_k^*}$$

is a measurement vector comprising the previously measured perceived sensitivity thresholds of the subset of test locations, wherein the previously measured perceived sensitivity thresholds of the subset of test locations are the elements of the vector.

That is, the estimates of the perceived sensitivity thresholds are derived by means of a pre-determined linear relationship between measured and estimated perceived sensitivity thresholds. This linear relationship is reflected by the coefficients of the reconstruction matrix. Stated another way, a set of linear functions between the measured perceived sensitivity thresholds of a given subset of the test locations and the estimates of the perceived sensitivity thresholds of all test locations of the plurality of test locations is provided, and the estimates are calculated from the set of linear functions using the measured perceived sensitivity values. The set of linear functions can be expressed mathematically as $$e_i = \sum_{j=1}^{S}$$

$\alpha_{ij} y_j$, wherein $e_i$ is the estimate of test location i, S is the number of previously measured test locations in the subset, $a_{ij}$ is a coefficient, and $y_j$ is a measured perceived sensitivity threshold at the test location j.

In certain embodiments, a final reconstruction matrix $\check{D}$ (corresponding to $$D_S^{I_S^*}$$

in the end) and the sequence $\Omega_S$ are determined (iteratively in particular) by means of a training matrix X having N columns and M rows, wherein each respective column of the training matrix X comprises a plurality of previously measured perceived sensitivity thresholds of a respective observer, wherein each perceived sensitivity threshold has been measured at a respective test location, and wherein a measurement matrix $Y_{\Omega_S}$, is provided, wherein the measurement matrix $Y_{\Omega_S}$ is a sub-matrix of the training matrix, wherein the rows of the measurement matrix $Y_{\Omega_S}$ are identical to or a noisy version of the rows of the training matrix indexed by the sequence $\Omega_S$, and wherein the final reconstruction matrix $\check{D}$ and the sequence $\Omega_S$ are determined such that an error $$\left\| X - \check{D} Y_{\Omega_S} \right\|_2^2$$

is minimized. Therein the expression $$\left\| X - \check{D} Y_{\Omega_S} \right\|_2^2$$

designates the L2-matrix norm of the difference between the training matrix X and the matrix product of the reconstruction matrix $\check{D}$ and the measurement matrix $Y_{\Omega_S}$.

Herein, the notion "noisy" refers to any variation of the rows of the training matrix that can be used in the process described herein. Particularly, as a noisy version of the rows of the training matrix low-quality data can be used, coming e.g. from a low quality data acquisition process.

In other words, the reconstruction matrix and the sequence are varied, wherein the argument of the minimum of the error is selected. In particular, this optimization is performed during a training phase prior to an examination phase, in which the perceived sensitivity thresholds of the observer are measured and the visual field map of the observer is obtained by the method according to the invention.

The elements in each respective column of the training matrix are previously measured perceived sensitivity thresholds of a respective data set, wherein the rows of the training matrix represent the test locations. Therein, each data set may correspond to a respective observer.

In particular, the measurement matrix is defined by the formula $Y_{\Omega_S} = I_{\Omega_S} X$, wherein $(I_{\Omega_S})_{i,j}=1$ in case the ith element of the sequence $\Omega_S$ equals the jth element of a sequence $\Omega$ of all test locations, and wherein $(I_{\Omega_S})_{i,j}=0$ otherwise.

In certain embodiments, the reconstruction matrix D and the sequence $\Omega_S$ are determined by providing an initial sequence $\Omega_{k-1, l}$ and an initial measurement matrix $Y_{\Omega k-1, l}$, wherein the initial measurement matrix $Y_{\Omega k-1, l}$ is either a sub-matrix of the training matrix X, wherein the rows of the initial measurement matrix $Y_{\Omega k-1,\ l}$ are identical to the rows of the training matrix X indexed by the initial sequence $\Omega_{k-1,\ l}$ or is a noisy version of the rows of the training matrix X indexed by the initial sequence $\Omega_{k-1,\ l}$, and wherein an element $$l_k^*$$

is added to the initial sequence $\Omega_{k-1,\ l}$, resulting in an updated sequence, wherein the element $$l_k^*$$

is the argument of the minimum of the expression $$\|X - D_k^l Y_{\Omega_{k-1,l}}\|_2^2,$$

wherein $$D_k^l$$

is a basis matrix defined by $$D_k^l = XY_{\Omega_{k-1,l}}^T\left(Y_{\Omega_{k-1,l}}Y_{\Omega_{k-1,l}}^T\right)^{-1},$$

wherein $$Y_{\Omega_{k-1,l}}^T$$

designates the transposed initial measurement matrix, and wherein $$\left(Y_{\Omega_{k-1,l}}Y_{\Omega_{k-1,l}}^T\right)^{-1}$$

designates the inverse matrix of the matrix product $$Y_{\Omega_{k-1,l}}Y_{\Omega_{k-1,l}}^T.$$

In contrast to a "brute-force" approach, where every possible sequence of test locations is tested, the previously described embodiment represents a so-called "greedy approach" which searches for a good sequence by sequentially selecting locations rather than trying to find them in one step.

In particular, the initial measurement matrix $Y_{\Omega_{k-1,\ l}}$ is defined as $Y_{\Omega_{k-1,\ l}}=I_{\Omega_{k-1,\ l}}X$, wherein $(I_{\Omega_{k-1,\ l}})_{i,\ l}=1$ in case the ith element of the initial sequence equals the jth element of the first sequence, and $(I_{\Omega_{k-1,\ l}})_{i,j}=0$ otherwise.

In certain embodiments, the at least one light signal comprises a first light signal and a subsequent second light signal, wherein the method comprises monitoring whether the observer has observed the first light signal and monitoring whether the observer has observed the second light signal, wherein in case the observer has not observed the first light signal, the light intensity value of the second light signal is increased compared to the light intensity value of the first light signal, and wherein in case the observer has observed the first light signal, the light intensity value of the second light signal is decreased compared to the light intensity value of the first light signal.

In certain embodiments, in case the observer has not observed the first light signal and the observer has observed the second light signal or in case the observer has observed the first light signal and the observer has not observed the second light signal, the perceived sensitivity threshold of the respective test location is assigned the light intensity value of the second light signal.

In certain embodiments, the light intensity value of the second light signal is increased or decreased by a first difference, wherein the at least one light signal comprises a third light signal provided subsequently to the second light signal, wherein in case the observer has not observed the second light signal, the light intensity value of the third light signal is increased by a second difference compared to the light intensity value of the second light signal, and wherein in case the observer has observed the second light signal, the light intensity value of the third light signal is decreased by the second difference compared to the light intensity value of the second light signal, wherein the second difference equals the first difference multiplied by a factor, wherein particularly the factor is 2.

In certain embodiments, in case the observer has not observed the second light signal and the observer has observed the third light signal, or in case the observer has observed the second light signal and the observer has not observed the third light signal, the perceived sensitivity threshold of the respective test location is assigned the light intensity value of the third light signal.

Such a strategy is also termed SORS-Dynamic strategy.

In certain embodiments, a respective initial probability mass function $$PMF^{l_{k+1}^*}$$

encoding a probability to have a certain perceived sensitivity threshold defined by the formula $$PMF^{l_{k+1}^*} = G(\mu, \sigma_l^2) + \alpha G(0, 1) + \epsilon_l,$$

is provided for each test location of the subset of test locations, wherein $$G(\mu, \sigma_l^2)$$

is a first Gaussian function, wherein μ designates a mean of the first Gaussian function, and wherein $$\sigma_l^2$$

designates a standard deviation of the first Gaussian function, and wherein G(0,1) is a second Gaussian function having a mean of 0 and a standard deviation of 1, and wherein $\alpha$ is a weight parameter between 0 and 1, in particular corresponding to a fraction of the population having an abnormal visual field, more particularly glaucomatous population, and wherein $\alpha_l$ is a constant representing a bias term to guarantee that no value is assigned zero probability, wherein particularly before measuring the at least one perceived sensitivity threshold, the mean $\mu$ of the first Gaussian function is assigned an age-matched normative value $nv_l$ of the perceived sensitivity threshold at the respective test location, and wherein after obtaining at least one perceived sensitivity threshold, the mean $\mu$ of the first Gaussian function is assigned the previously derived estimate of the perceived sensitivity threshold of the respective test location, and wherein the first light signal is provided at a light intensity value which is equal to the mean of the first Gaussian function, and wherein after monitoring whether the observer has observed the first light signal, an updated probability mass function is derived by multiplying the initial or previous updated probability mass function by a likelihood function, particularly having a sigmoidal shape, wherein the likelihood function is monotonously increasing in case the observer has observed the light signal, and wherein the likelihood function is monotonously decreasing in case the observer has not observed the light signal, and wherein the second light signal is provided at a light intensity value which is equal to the mean of the updated probability mass function. This embodiment of the method is also termed SORS-ZEST using the ZEST method (King-Smith P E, Grigsby S S, Vingrys A J, Benes S C, Supowit A. *Efficient and unbiased modifications of the QUEST threshold method: theory, simulations, experimental evaluation and practical implementation. Vision research.* 1994; 34(7):885-912) at individual locations. Therein, a so-called Bayesian update of the probability mass function is performed by multiplying the prior probability mass function with a likelihood function (for example probability-of-seeing-curve) representing a yes-answer or a no-answer depending on whether the observer has observed the light signal.

In certain embodiments, in case a standard deviation of the updated probability mass function is larger than or equal to a first stop value, particularly 2, a further light signal (comprised in the at least one light signal) is provided, particularly at an intensity value equal to the mean of the updated probability mass function, wherein the method comprises monitoring whether the observer has observed the further light signal, and wherein a further updated probability mass function is generated by multiplying the previous probability mass function with a likelihood function, wherein the likelihood function is monotonously increasing in case the observer has observed the further light signal, and wherein the likelihood function is monotonously decreasing in case the observer has not observed the further light signal, and wherein in case the standard deviation of the updated probability mass function is smaller than the first stop value, the sensitivity estimate of the respective test location is assigned the value of the mean of the updated probability mass function.

In certain embodiments, in case the total number of light signals provided at the respective test location is smaller than or equal to a second stop value, particularly 4, a further light signal is provided at the respective test location, and the method comprises monitoring whether the observer has observed the further light signal.

BRIEF DESCRIPTION OF THE DRAWINGS

The invention is further described by means of Figures and examples, from which additional embodiments can be drawn.

EXAMPLE

Perimetry testing, such as standard automated perimetry (SAP) is an automated method to measure visual function and is used for diagnosing ophthalmic and neurological conditions. Its working principle is to sequentially query a subject (also termed observer) about perceived light using different brightness levels at different visual field locations (also termed test locations). At a given test location, a perceived sensitivity threshold (PSTs) is measured, wherein the perceived sensitivity threshold is defined as the stimulus intensity which is observed and reported 50% of the time (in other words at 50% probability) by the observer.

Figure 1:
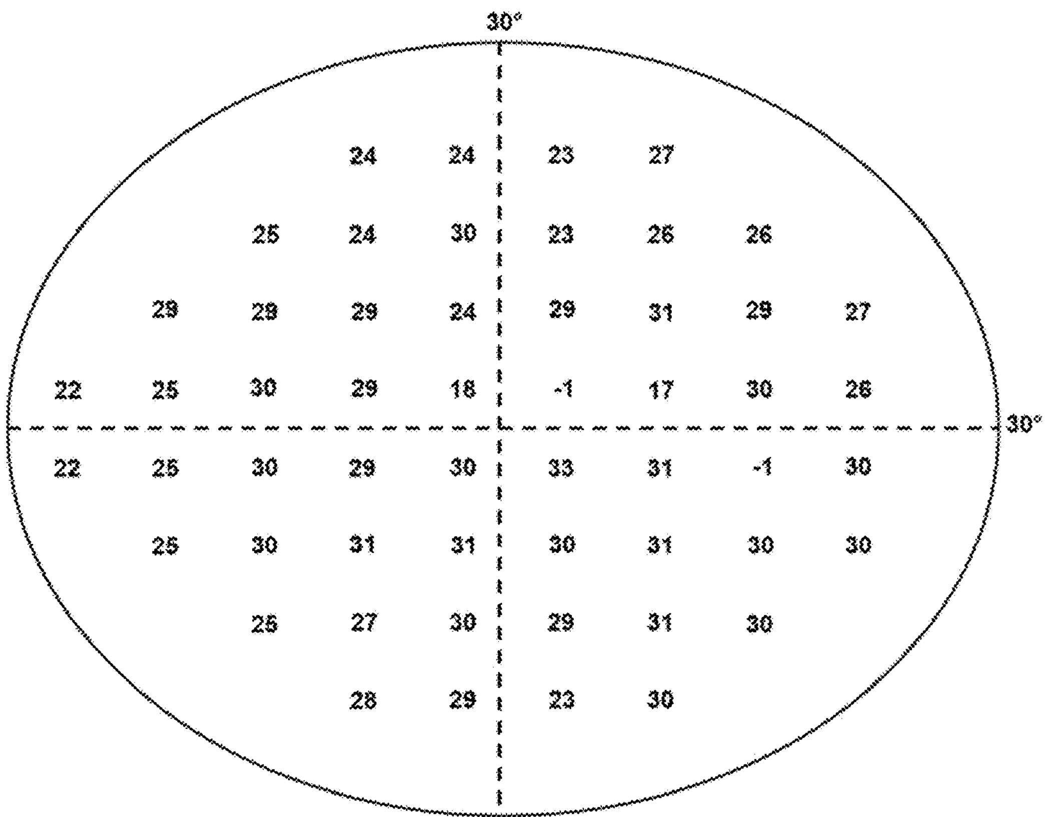
FIG. 1 shows a visual field with perceived sensitivity thresholds (PSTs) at locations in the central 30° field.
Figure 2:
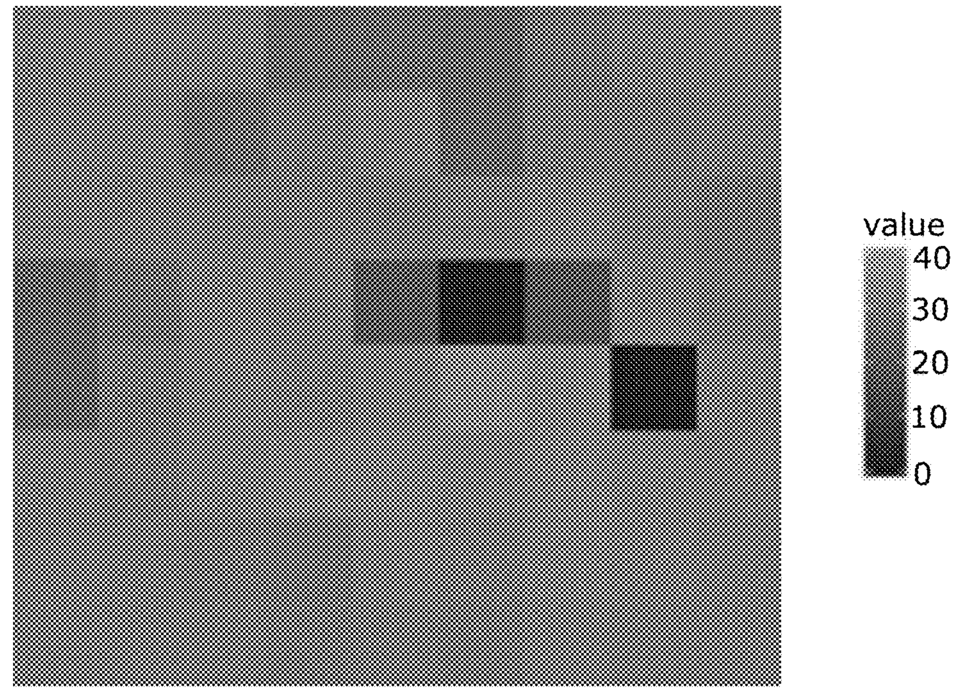
FIG. 2 shows an associated image representation of the visual field shown in FIG. 1. Dark regions correspond to visual defects.
Figure 3:
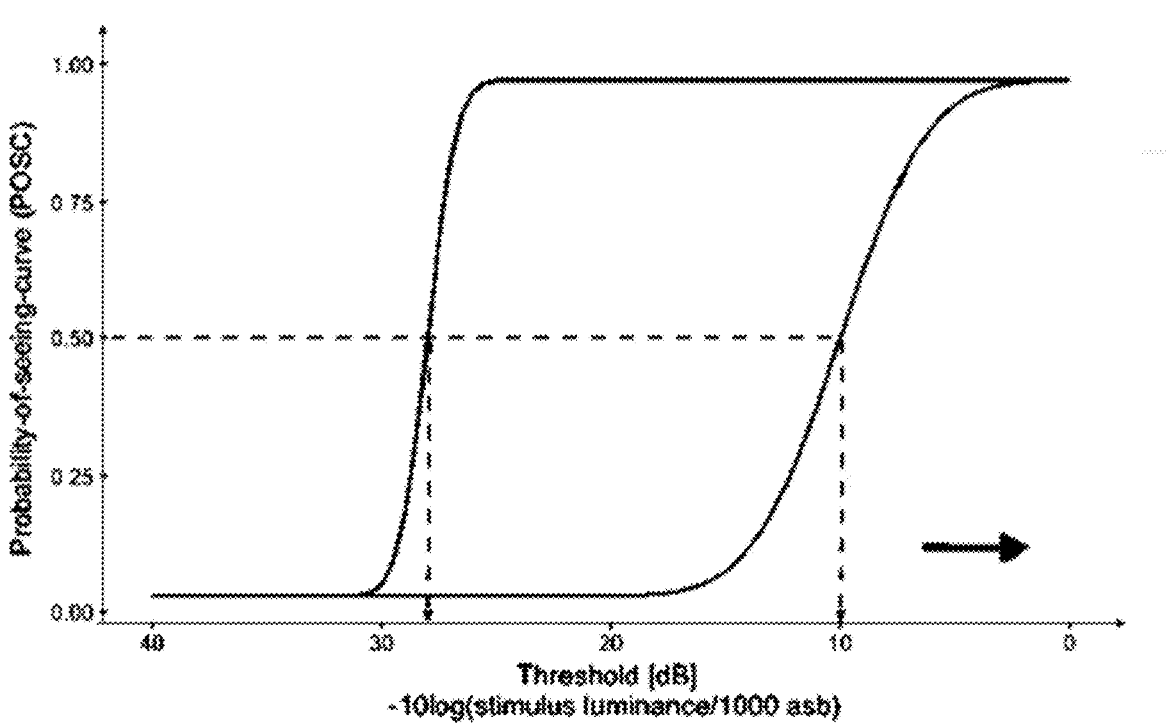
FIG. 3 shows a probability-of-seeing-curve. The probability of seeing a stimulus increases with increasing stimulus luminance. Note the inverse relationship between sensitivity thresholds and stimulus luminance.

The goal of perimetry is to estimate the perceived sensitivity thresholds at M locations (e. g., M=54 as in FIG. 1 describing the visual field. The perceived sensitivity threshold at an individual location corresponds to the sensitivity threshold, in dB, for which there is a 50% probability chance of being observed. Traditionally, this has been modeled using a probability-of-seeing-curve (POSC) such as the one illustrated in FIG. 3. As such, the response distribution is of maximum entropy, as the likelihood of observing an incorrect response (i. e., a false positive or false negative) is maximal at the perceived sensitivity threshold value. In addition, at unhealthy locations with lower perceived sensitivity threshold, the number of incorrect answers is expected to increase as the probability-of-seeing-curve becomes more gradual (e. g., right curve in FIG. 3).

To estimate visual fields using standard automated perimetry, different automated methods are known from the prior art. Each of them can be characterized as methods that include the following: (1) a method to determine what initial intensity should be shown when testing a given location, (2) a local perceived sensitivity threshold testing strategy that determines what intensities should be presented over time at a given location and (3) a strategy for selecting the order in which different locations are evaluated.

From this, a number of methods have been proposed in order to produce accurate or approximate visual fields. The simplest method is the Full-Threshold (FT) strategy used in large clinical trials. It evaluates each location in a random order using a predefined staircase intensity sequence (e. g., increase or decrease the intensity based on the previous response) starting from population normal values. FT is extremely accurate as it presents many stimuli but inevitably leads to longer examination times, ranging from 12 to 18 minutes per eye.

An alternative is the Zippy Estimation by Sequential Testing (ZEST), which unlike FT, avoids a predefined staircase and opts for a sequential Bayesian model to select likely perceived sensitivity threshold values. As such, it highly depends on a probability mass function (PMF) over the sensitivity thresholds for a given location in order to compute posterior distributions of perceived sensitivity threshold. ZEST evaluates all visual field locations in a random order, yet has been found to effectively reduce the number of presentations thanks to the Bayesian principle.

A variation of FT is also the Dynamic Test Strategy (DTS) which uses a staircasing approach with adaptive step sizes that are determined by the slope of the probability-of-seeing-curve. Accordingly, larger step sizes are used for depressed perceived sensitivity threshold areas where the probability-of-seeing-curve is wider. All locations are tested but each starting intensity is based on a local average of found perceived sensitivity thresholds. In general, DTS reduces testing time on average by 40% compared to FT with a reasonable visual field approximation and is a standard of care in many eye clinics and hospitals. Tendency Oriented Perimetry (TOP) on the other hand uses an asynchronous staircasing approach with deterministic steps at individual locations such that each location is only tested once. Locations in groups of four are tested group by group; once one group of test locations is tested, the estimates of the locations in the other groups are updated by averaging the estimates at their already-tested-neighboring locations. The updated estimates are then used as the starting points for querying the next group of locations. As TOP only presents one stimulus per location, it results in a very fast but error prone estimation procedure.

One common aspect of the presented approaches so far is that they all test the available locations at least once and have a subject feedback on each of them. More recently, Spatial Entropy Pursuit (SEP) combines the ZEST method and a graphical model to reduce the examination time. It uses a combined entropy and gradient heuristic to adaptively select what locations should be tested within a probabilistic model. In addition, unlike the previously mentioned strategies, it is able to ignore some locations that are deemed certain even though they have not been explicitly tested. SEP is reported to reduce the number of stimuli by 55% for healthy subjects and by 23% for glaucomatous subjects when compared to DTS. A limitation of SEP however is its sensitivity to the selected graphical model and ZEST parameters. It therefore requires a rigorous parameter optimization to perform at an effective level.

Overall, while some of the aforementioned methods are used in clinical care (i. e., DTS, FT and TOP), they remain inadequate in terms of speed, accuracy and/or feasibility.

Given this inherently time-intensive and noisy process, fast testing strategies are necessary in order to measure existing regions more effectively and reliably.

We now describe our method, SORS, which treats the problem of visual field estimation as a reconstruction problem from sparse observations. In this setting, the observations will be a small or limited number of visual field locations that have been viewed to a satisfactory accuracy using either a traditional staircasing method as that in DTS or in ZEST. Using these locations and their perceived sensitivity thresholds, we will leverage the correlative nature of the locations within a training data set to estimate the perceived sensitivity thresholds at unobserved locations of the visual field. As such, SORS can be split into two sections:

1. Training phase: From a dataset of fully observed visual fields, we will determine which locations are most effective to reconstruct the entire visual field from partial observations and simultaneously compute optimal reconstruction coefficients. This will be performed for an increasing number of observed locations in a greedy manner.
2. Examination phase: For a new examination, found locations and reconstruction coefficients will be used to infer unobserved locations. If the user prefers a more accurate estimate, further locations can be observed using previously estimated perceived sensitivity thresholds as starting points and the reconstruction can be recomputed.

We now specify some notation that will be necessary throughout the remainder of the example.

Notation: Let $X \in R^{M \times N}$ be a matrix of N visual fields where the nth column vector, $x_n \in R^M$, n=1, . . . , N, corresponds to a visual field with M perceived sensitivity threshold entries. The ordering of visual field locations is kept constant for all N samples and is denoted by the sequence $\Omega$=[1, . . . M]. While $\Omega$ is a sequence, we will slightly abuse this notation and use set operators on n as well. We define S≤M to be the number of observed visual field locations tolerated during an examination and let $\Omega_S \in \Omega$ be the sequence of such observed location indices. Our assumption is that $\forall n$, $x_n$ can be estimated by a linear combination of its observed entries using a basis matrix $D \in R^{M \times S}$ that defines the linear relationship between test locations.

Training phase Assuming that perceived sensitivity thresholds are linearly-dependent to each other and that an examination allows for up to S observations to be made, we can approximate the training set X by computing $$\hat{X} = DY_{\Omega_S}, \tag{1}$$

where $\hat{X}$ is an approximate reconstruction of the visual fields X and $Y_{\Omega_S} = I_{\Omega_S} X$ such that $$(I_{\Omega_S})_{i,j} = 1 \text{ if } (\Omega_S)_i = (\Omega)_j, \text{ and } (I_{\Omega_S})_{i,j} = 0 \text{ otherwise}, \tag{2}$$

where $I_{\Omega_S} \in R^{S \times M}$ and $(\Omega_S)_i = (\Omega)_j$ indicates that the ith measurement corresponds to the location j. By this, the measurement matrix $Y_{\Omega_S}$ is a sub-matrix of X consisting of rows indexed by $\Omega_S$.

Recall that we are interested in finding an optimal sequence of S locations to evaluate and a corresponding basis that would lead to a good estimate $\hat{X}$. We thus cast this as an optimization problem of the following form, $$\{D^*, \Omega_S^*\} = \text{argmin}_{D \in R^{M \times S}, \Omega_S \in \Omega} \|X - DY_{\Omega_S}\|_2^2. \tag{3}$$

Note that solving Eq. 3 by brute-force suggests optimizing iteratively over D for every possible sequence $\Omega_S$, which is not feasible as the number of available sequences could be very large depending on S.

Alternatively, we propose a greedy approach which searches for a good subset $\Omega_S$ by sequentially selecting locations rather than trying to find them in one step. Formally, the kth element in $$\Omega_S = \{l_1^*, l_2^*, \ldots, l_S^*\}$$

is found by $$l_k^* = \text{argmin}_{l \in \Omega \backslash \Omega_{k-1}} \|X - D_k^l Y_{\Omega_{k-1,l}}\|_2^2, \; k = 1, \ldots, S, \tag{4}$$

where $$D_k^l = XY_{\Omega_{k-1,l}}^T \left(Y_{\Omega_{k-1,l}} Y_{\Omega_{k-1,l}}^T\right)^{-1} \tag{5}$$

is a basis matrix associated with the measurement matrix $Y_{\Omega_{k-1,l}}$, $\Omega_{k-1,l}$ is the sequence $\Omega_{k-1,l}$ to which location l is appended at the end and $\Omega_0 = \theta$. As the intermediate basis matrices will be also used at examination time, the procedure results in both the sequence $$\Omega_S^* = \{l_1^*, l_2^*, \ldots, l_S^*\}$$

and the corresponding basis set $$D^* = \left\{D_k^{l_k^*}\right\}, \; k = 1, 2, \ldots, S.$$

We summarize the training phase algorithm o SORS in the following Algorithm 1:

| Algorithm 1: SORS Training algorithm |
|---|
| Data: Training data X, $\Omega$ |
| Initialize $\Omega_S^* = \emptyset$, $D^* = \emptyset$, $\Omega_0 = \emptyset$, $I_{\Omega_S} = 0$; |
| for k = 1,2, . . . , S do |
|     $\text{error}_l \leftarrow 0, \forall l \in (\Omega \backslash \Omega_S)$ |
|   for $l \in (\Omega \backslash \Omega_S)$ do |
|       $\Omega_{k-1,l} \leftarrow \Omega_{k-1} \cup \{l\}$ |
|       $Y_{\Omega_{k-1,l}} \leftarrow I_{\Omega_{k-1,l}} X$ |
|       $D_k^l \leftarrow XY_{\Omega_{k-1,l}}^T (Y_{\Omega_{k-1,l}} Y_{\Omega_{k-1l}}^T)^{-1}$ |
|       $\hat{X} \leftarrow D_k^l Y_{\Omega_{k-1,l}}$ |
|       $\text{error}_l \leftarrow \|X - \hat{X}\|_2^2$ |
|   end |
|       $l_k^* \leftarrow \arg\min_l \text{error}_l$ |
|       $\Omega_S^* \leftarrow \Omega_S^* \cup l_k^*$ |
| $D^* \leftarrow D^* \cup D_k^{l_k^*}$ with $D_k^{l_k^*} = XY_{\Omega_{S^*}}^T (Y_{\Omega_{S^*}} Y_{\Omega_{S^*}}^T)^{-1}$ |
| end |
| Result: Sequence $\Omega_S^*$, Basis set $D^*$ |

While the presented greedy approach presumably leads to sub-optimal solution, we show that it provides superior performances over potential alternative schemes.

Examination phase During an examination, the location ordering $$\Omega_S^*$$

is sequentially evaluated using either the staircasing or Bayesian approach for perceived sensitivity threshold estimation. In the following, we detail this process and state how either location testing strategy can be used. In general, we perform the following two steps iteratively for S locations using either perceived sensitivity threshold estimation method, which we denote here as P:

1. Location $$k \in [1, S], l_k^*$$

of an unknown visual field e is tested with P and the entire visual field is reconstructed using the corresponding basis, $$D_k^{l_k^*}$$

as given by $$\hat{e}_k = D_k^{l_k^*} y_{\Omega_k^*}, \tag{6}$$

where $$y_{\Omega_k^*}$$

is the observed measurement vector including all previous measurements at the locations $$l_1^*, l_2^*, \ldots, l_{k-1}^*$$

as well as at the last one, i.e., $$l_k^* \text{ and } \hat{e}_k$$

is the estimated visual field at the kth step. Note that all the previously tested k perceived sensitivity thresholds are used for this reconstruction step.

2. The initial threshold starting point for method P is updated at the unobserved location $$l_{k+1}^*$$

that is to be tested next using $\hat{e}_k$. As this process depends explicitly on P, we outline this more clearly for both staircasing and Bayesian methods below.

This two-step iterative process is stopped when all locations in $$\Omega_S^*$$

have been tested using P. Note that by updating the starting points for the next locations to query, we are able to further reduce the number of stimuli at a given location, as the presented stimulus is on average closer to the true perceived sensitivity threshold value. We now detail two versions of our method that use different perceived sensitivity threshold estimation strategies.

SORS-ZEST This version of SORS uses the ZEST Bayesian procedure when testing a single test location. As previously mentioned, ZEST starts testing a location according to a prior probability mass function (PMF) which is a weighted combination of normal and abnormal perceived sensitivity thresholds (Turpin A, McKendrick A M, Johnson C A, Vingrys A. J. *Properties of Perimetric Threshold Estimates from Full Threshold, ZEST, and SITA-like Strategies, as Determined by Computer Simulation. Investigative Opthalmology & Visual Science.* 2003:44(11):4787). In practice, this corresponds to a mixture of two Gaussian distributions centered on an age-matched normal value and on an abnormal value (0 in practice), representing healthy and glaucomatous population, respectively. This can be formulated as $$PMF^l \approx G(nv_l, \sigma_l^2) + \alpha G(0, 1) + \epsilon_l, \tag{7}$$

where $PMF^l$ is the PMF at location l, G is a Gaussian function with parameters being the mean and standard deviation, $nv_l$ is the age-matched normative value associated with location l, α is the weight of the Gaussian function corresponding to sick population, and $\epsilon_l$ is a bias term to guarantee that no value is assigned zero probability.

Given that in step 2 of the examination method, we can reconstruct visual fields from few observations using $$D_k^{l_k^*},$$

we propose an alternative prior distribution for each location to be tested that is shifting such that its mode is given by the value at the location $$l_{k+1}^*.$$

That is, we let $$PMF^{l_{k+1}^*} \approx G\left(\hat{e}_k^{l_{k+1}^*}, \sigma_l^2\right) + \alpha G(0, 1) + \epsilon_l, \tag{8}$$

where $$PMF^{l_{k+1}^*}.$$

is the prior PMF associated with location $$l^*_{k+1} \text{ and } \hat{e}_k^{l^*_{k+1}}$$

is the estimated value at the $$l^*_{k+1}$$

location of the last reconstructed visual field $\hat{e}_k$. Note that the first test location uses a standard prior PMF as given in Eq. 7 but that the following locations use adjusted PMFs according to the visual field reconstructed.

SORS-Dynamic In this version of SORS, we use a staircasing approach with step sizes that adapt to the slope of the probability-of-seeing-curve as in Dynamic Test Strategy (DTS). As we locally use the same procedure as DTS, we denote this version SORS-Dynamic where SORS mainly differs from DTS in the selection of locations to test, in the determination of the starting stimulus luminance and most importantly, in the number of test locations queried. In this method, the starting stimulus presented at the next location $$l^*_{k+1}$$

is given by $$\hat{e}_k^{l^*_{k+1}}$$

estimated during the kth reconstruction step.

Results The method of the present invention was validated using a publicly available visual field data set (Erler N S, Bryan S R, Eilers P H C, Lesaffre E M E H, Lemij H G, Vermeer K A. *Optimizing Structure-Function Relationship by Maximizing Correspondence Between Glaucomatous Visual Fields and Mathematical Retinal Nerve Fiber Models. Investigative Opthalmology & Visual Science.* 2014; 55(4):2350; Bryan S R, Vermeer K A, Eilers P H C, Lemij H G, Lesaffre E M E H. *Robust and Censored Modeling and Prediction of Progression in Glaucomatous Visual Fields. Robust and Censored Modeling of VFs. Investigative Ophthalmology & Visual Science.* 2013; 54(10):6694. doi: 10.1167/iovs.12-11185) containing 5108 visual fields from both eyes of 22 healthy and 139 glaucomatous patients. The data was collected using a Humphrey Visual Field Analyzer II (Carl Zeiss Meditec AG, Germany). Each visual field contains M=54 test locations.

To evaluate the performance of SORS in comparison to established methods, the method was compared to that of Zippy Estimates for Sequential Testing (ZEST; King-Smith P E, Grigsby S S, Vingrys A J, Benes S C, Supowit A. *Efficient and unbiased modifications of the QUEST threshold method: theory, simulations, experimental evaluation and practical implementation. Vision research.* 1994; 34(7):885-912.), Tendency Oriented Perimetry (TOP, Morales J, Weitzman M L, Gonzalez de la Rosa M. *Comparison between tendency-oriented perimetry (TOP) and octopus threshold perimetry. Ophthalmology.* 2000; 107(1):134-142.), Dynamic Test Strategy (DTS, Weber J, Klimaschka T. *Test time and efficiency of the dynamic strategy in glaucoma perimetry. German journal of ophthalmology.* 1995; 4(1): 25-31) and Spatial Entropy Pursuit (SEP, Wild D, Kucur Seda S, Sznitman R. *Spatial Entropy Pursuit for Fast and Accurate Perimetry Testing. Investigative Opthalmology & Visual Science.* 2017, in the following referenced as Wild et al., 2017'). All experiments were implemented using R and the Open Perimetry Interface (OPI), which allows us to simulate the response of individuals according to their true visual field.

We performed a 10-fold cross-validation; training and test visual fields in each fold were selected such that they do not include visual fields from the same patient. That led to folds with roughly 4597 training and 511 test samples. For each fold, the optimal sequence of test locations $$\Omega^*_S,$$

as well as the corresponding basis set D* were found for S=1, 2, . . . , 40 and evaluated on the test data. In addition, for each fold, we optimized the ZEST parameters related to the prior probability of each location, specifically $\sigma_l$ and $\epsilon_l$, while setting $\alpha$ to 0.1 in Eq. 7. We set the ZEST stopping criterion as the standard deviation of the posterior PMF being less than 2 and the maximum number of stimuli per location being 4. Below, we present the results for one fold selected at random, as similar trends are observed in other folds.

Qualitative evaluation We show experimentally on a visual field data set of both healthy and glaucomatous subjects, that our strategy provides large speed gains compared to existing methods without compromising the accuracy of estimated visual fields. In addition, we show that although our strategy does not require all locations to be tested, it allows for good accuracy even in cases of local visual impairment.

Figure 4:
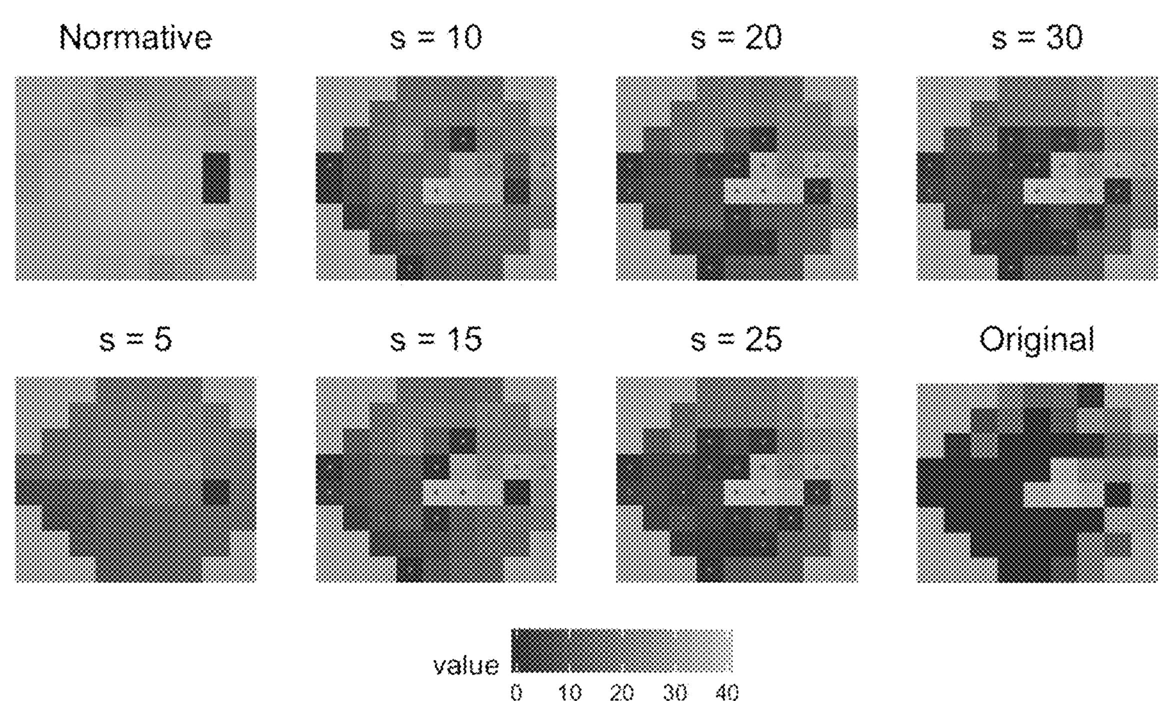
FIG. 4 shows qualitative evaluation of SORS. Top left shows the starting visual field with age-normalized values. Bottom right shows the true visual field to be estimated. In between, the sequentially estimated visual fields using $S \in \{5, 10, 15, 20, 25, 30\}$ location measurements. Points show the corresponding S tested locations.
Figure 5:
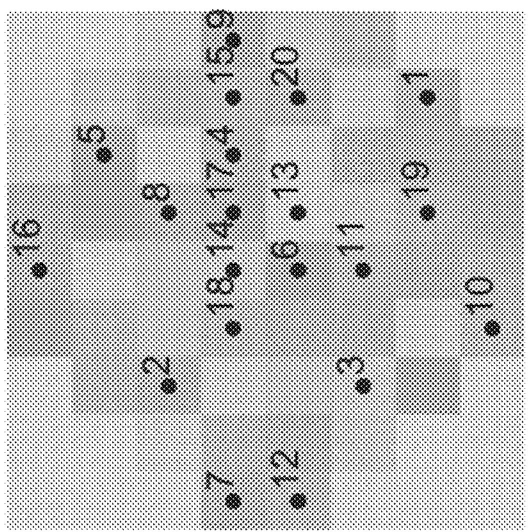
FIG. 5 shows optimal test locations found by SORS Optimal test locations when trained on healthy (left), glaucomatous (middle) and mixed population (right) are presented. Numbers show the order in which the locations are evaluated.
Figure 5:
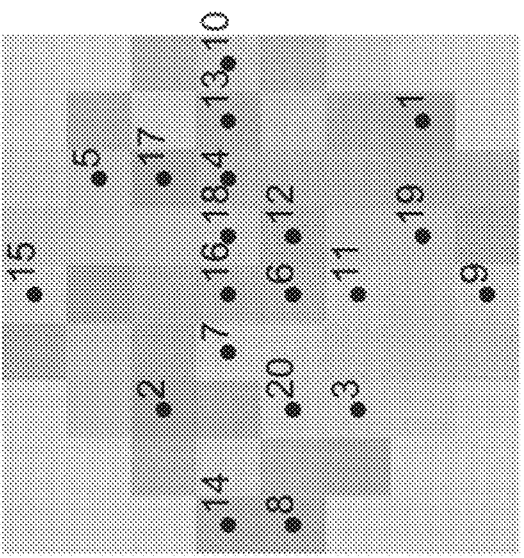
Figure 5:
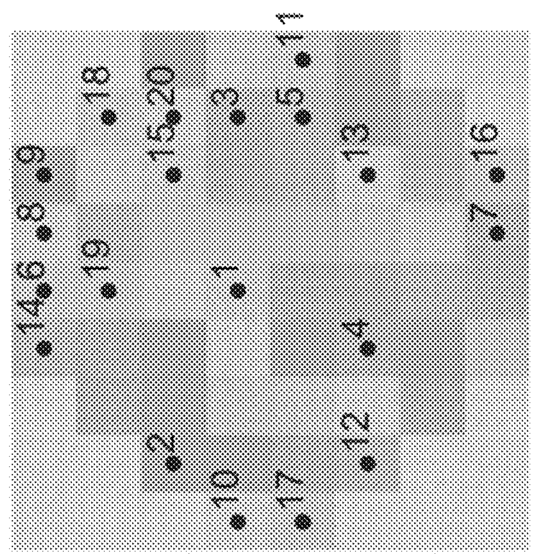

We first show in FIG. 4 an example of an examination and how SORS sequentially evaluates different locations. In each field, perceived sensitivity threshold values are estimated (dark regions indicating defects) and dots show tested locations. As more test locations are used, differences between the true and estimated perceived sensitivity threshold values decrease and a reasonable estimation is achieved with only 15-20 locations tested. Note that even if not all locations are evaluated, the visual field estimate is close to the true visual field (see S=25). Similarly, FIG. 5 depicts the order of the 20 first locations selected as a function of the training set used. In particular we show different orderings found when training using only healthy subjects (left), glaucoma patients (middle) and a mixed population of both subjects (right). Note that the mixed population ordering is similar to that of the glaucoma patient ordering, because the number of healthy subjects is an order of magnitude smaller than that of glaucoma patients. Importantly, there is a significant difference in selected locations between healthy and glaucomatous individuals. It can be seen, that training on healthy subjects leads to more locations selected at the periphery of the visual field. This is in strong contrast to a concentrated set of central locations when training with glaucomatous subjects.

Figure 6:
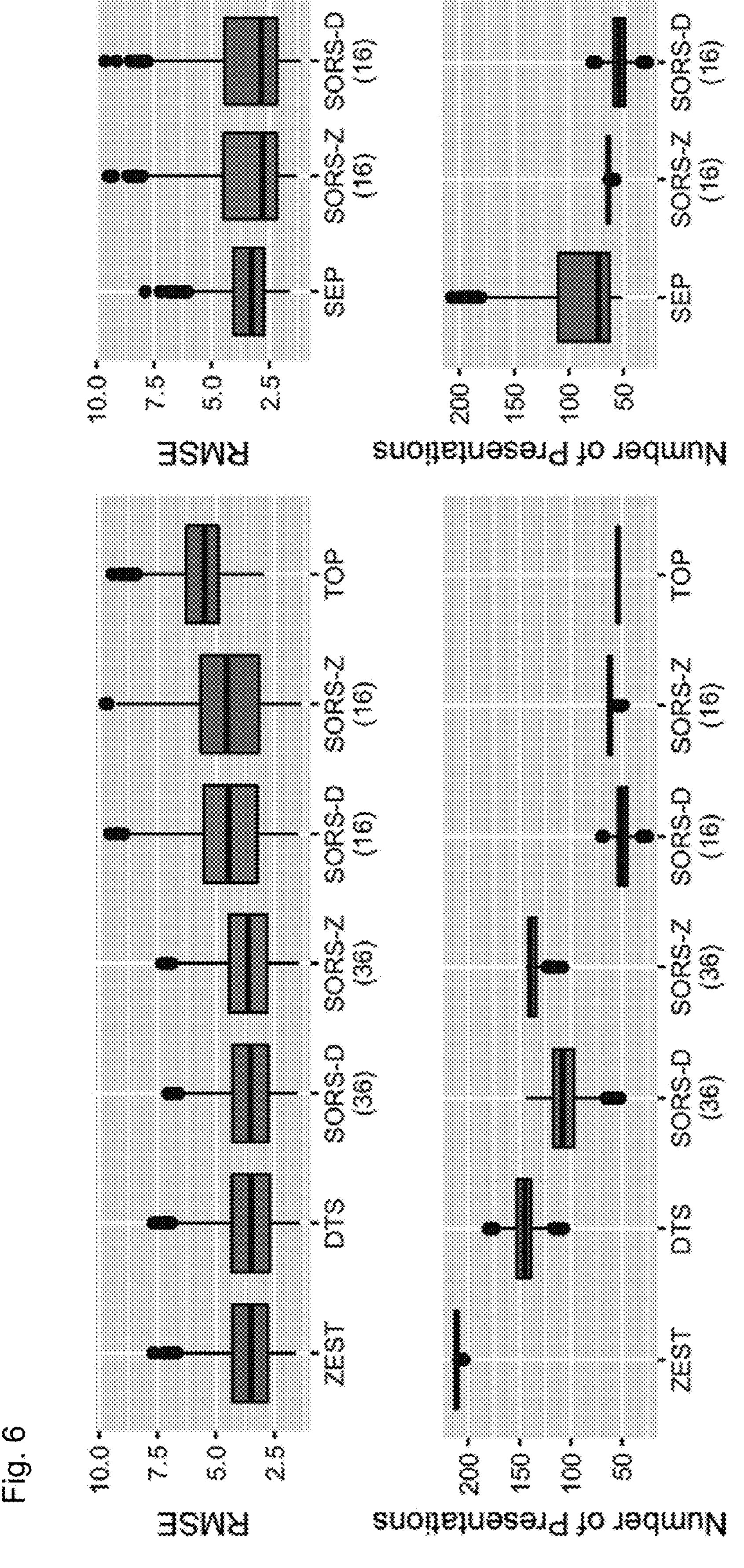
FIG. 6 shows performance benchmarking with the state-of-the-art perimetry strategies. SORS is compared to (left) existing and commercially used methods, (right) to Spatial Entropy Pursuit (SEP) on mixed population. SORS is evaluated on 16 and 36 locations as specified in parenthesis. SORS-D and SORS-Z stand for SORS-Dynamic and SORS-ZEST, respectively.

Accuracy and speed performance comparison FIG. 6 presents quantitative performances of the evaluated methods in terms of Root Mean Square Error (RMSE) and the number of stimuli presentations used (i. e., examination time). In the figures, SORS-D and SORS-Z stand for SORS-Dynamic and SORS-ZEST, respectively.

FIG. 6 (left) compares the performance of SORS with S=16 and S=36 with that of state-of-the-art strategies. With 54 stimuli presentations, TOP achieves relatively low accuracy (median RMSE of 5.47). Testing only 16 locations, SORS-D (median RMSE of 4.47, median number of presentations of 50) performs significantly better than TOP in both accuracy and speed (Mann-Whitney U test, $p<0.0001$). Similarly, SORS-Z testing only 16 locations (median RMSE of 4.52, median number of presentations of 62) has a reduced RMSE compared to TOP (significant difference, Mann-Whitney U test, $p<0.0001$), with a slightly higher number of presentations.

Testing 36 locations, SORS-D (median RMSE of 3.54) and SORS-Z (median RMSE of 3.63) achieves similar performance to DTS (median RMSE of 3.51, non-significant difference with SORS-D, Mann-Whitney U test, $p>0.05$, significant difference with SORS-Z, Mann-Whitney U test, $p<0.001$) and ZEST (median RMSE of 3.51, Mann-Whitney U test, $p>0.05$). At similar visual field estimate accuracy, SORS methods require fewer stimuli presentations than DTS and ZEST. More specifically, when compared to ZEST (median number of presentations of 211), SORS-Z (median number of presentations of 140) achieves the same accuracy (non-significant difference, Mann-Whitney U test, $p>0.05$) with approximately 34% fewer number of stimuli presentations. Similarly, SORS-D (median number of stimuli presentations 145) achieves the same RMSE performance with DTS (median number of stimuli presentations 145, non-significant difference, Mann-Whitney U test, $p>0.05$) by reducing 25% of the required stimuli presentations (significant difference, Mann-Whitney U test, $p<0.0001$).

These results support the fact that SORS can speed up examinations more than other state-of-the-art approaches. In addition, our methods have less variance in the produced visual fields as evaluated in test-retest experiments and perform well when testing on only healthy or glaucomatous populations (see below).

To fairly compare SORS to SEP, we run experiments on the same training and test sets that were used in Wild et al., 2017 and show the results in FIG. 6 (right). First, one should note that as the test data set in this experimental set-up has 245 healthy and 172 glaucomatous visual fields, SORS-Z (median RMSE of 2.79 and median number of stimuli presentations of 64) and SORS-D (median RMSE of 2.85 and median number of stimuli presentations of 54) have lower RMSE and number of stimuli presentations than that shown in FIG. 6 (left) where test set includes 32 healthy and 465 glaucomatous visual fields. Accordingly, when testing 16 locations, SORS-Z and SORS-D yield on average more accurate and faster examinations than SEP (median RMSE of 3.27 and median number of stimuli presentations of 73, Mann-Whitney U test, $p<0.0001$). In addition, the comparison between SEP and SORS-Z is interesting as they can both be seen as meta-strategies employing the same Bayesian scheme at individual perceived sensitivity threshold visual field locations. The fact that SORS-Z outperforms SEP supports that SORS can encode and leverage relationships between visual field locations, without the need of modeling the location relationships explicitly.

Figure 7:
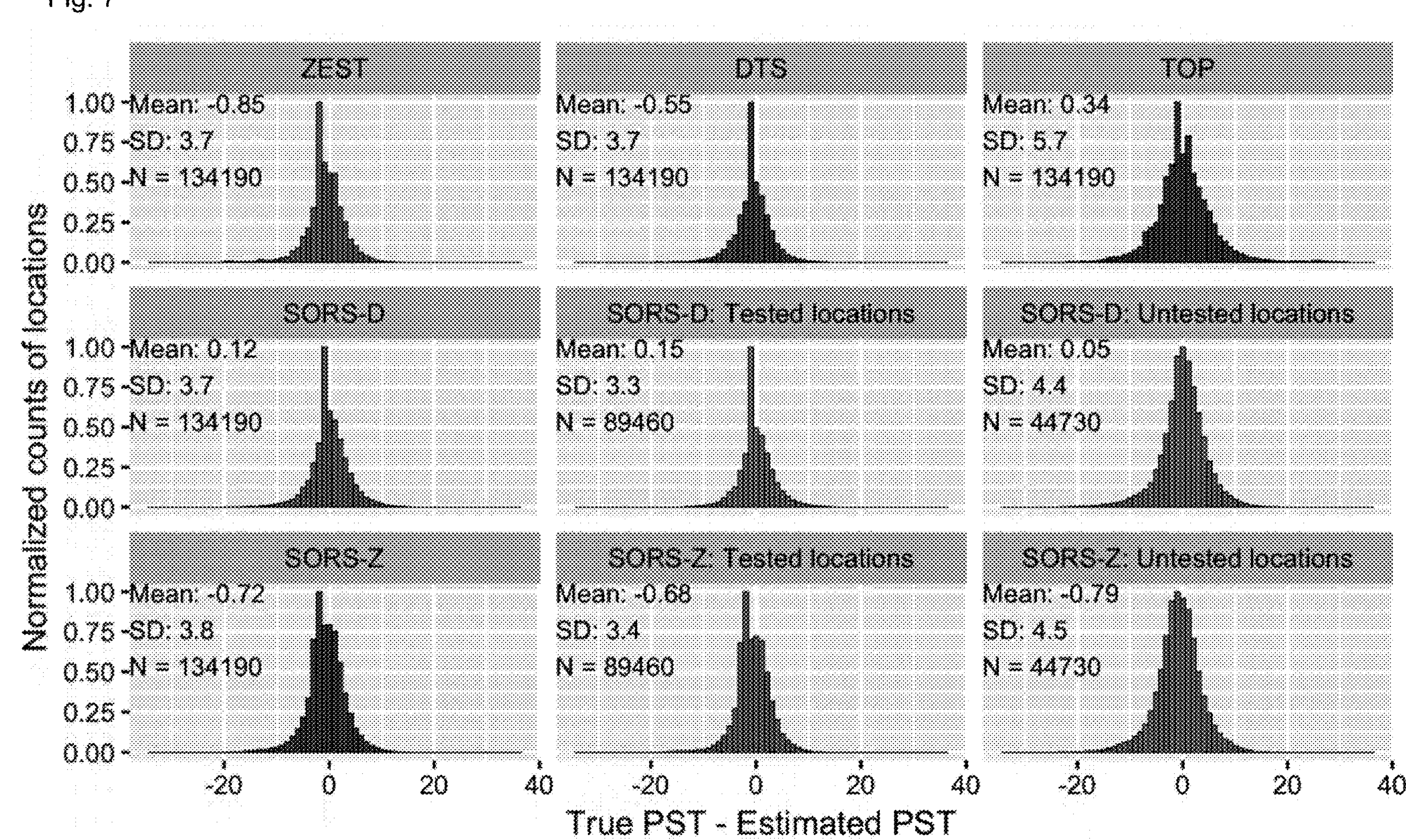
FIG. 7 shows a normalized histogram of signed errors of all visual field locations. Mean, standard deviations (SD) and number of visual field locations (N) per plot are given in the left top corner of each plot. Histograms of errors on tested and untested locations are separately shown for SORS-Z and SORS-D.

Error and estimation bias To quantify the distribution of errors in the estimation process of the tested perimetry strategies, FIG. 7 depicts the histogram of the average signed estimation error per location for ZEST, DTS, SORS-D and SORS-Z. For SORS-Z and SORS-D, we also separately provide error histograms for locations that have been observed and those that have been inferred.

Accordingly, SORS-D leads to the smallest bias when the absolute mean of the distributions is considered. Furthermore, it is biased towards lower values as the mean of the distribution is positive, whereas all other methods except TOP are biased towards higher values. Typically, lower value biases are preferable since they carry less patient risk than higher value bias. Interestingly, SORS-D uses the same location perceived sensitivity threshold estimation scheme than DTS, yet there is a noticeable reduction in the RMSE. The contribution of SORS is more obvious when DTS is compared to SORS-D at observed locations. This indicates that the way SORS selects test locations and estimates the next query stimulus is more favorable than that of DTS. As for SORS-Z, it is biased towards higher estimations than the true perceived sensitivity threshold values, showing resemblance to ZEST's behavior, with a slight reduction in mean RMSE and bias. When we compare the error histograms of untested and tested locations for SORS-D, the bias is reduced with an increase in the standard deviation. This is expected as the variance in the estimation of untested locations is likely to be higher. As expected, SORS-Z has stronger bias towards over-estimation for untested locations than tested locations. The tendency of SORS-Z/ZEST to over-estimate in general is most likely due to sub-optimal configuration of Bayesian perceived sensitivity threshold estimation as discussed in Wild et al., 2017. However, even with sub-optimal parameters, SORS-Z has a comparable and even better performance on average compared to state-of-the-art methods. Moreover, both SORS-Z and SORS-D have preferable error performances compared to TOP which leads to a higher error SD, much higher than SORS's error SDs at untested locations.

Figure 8:
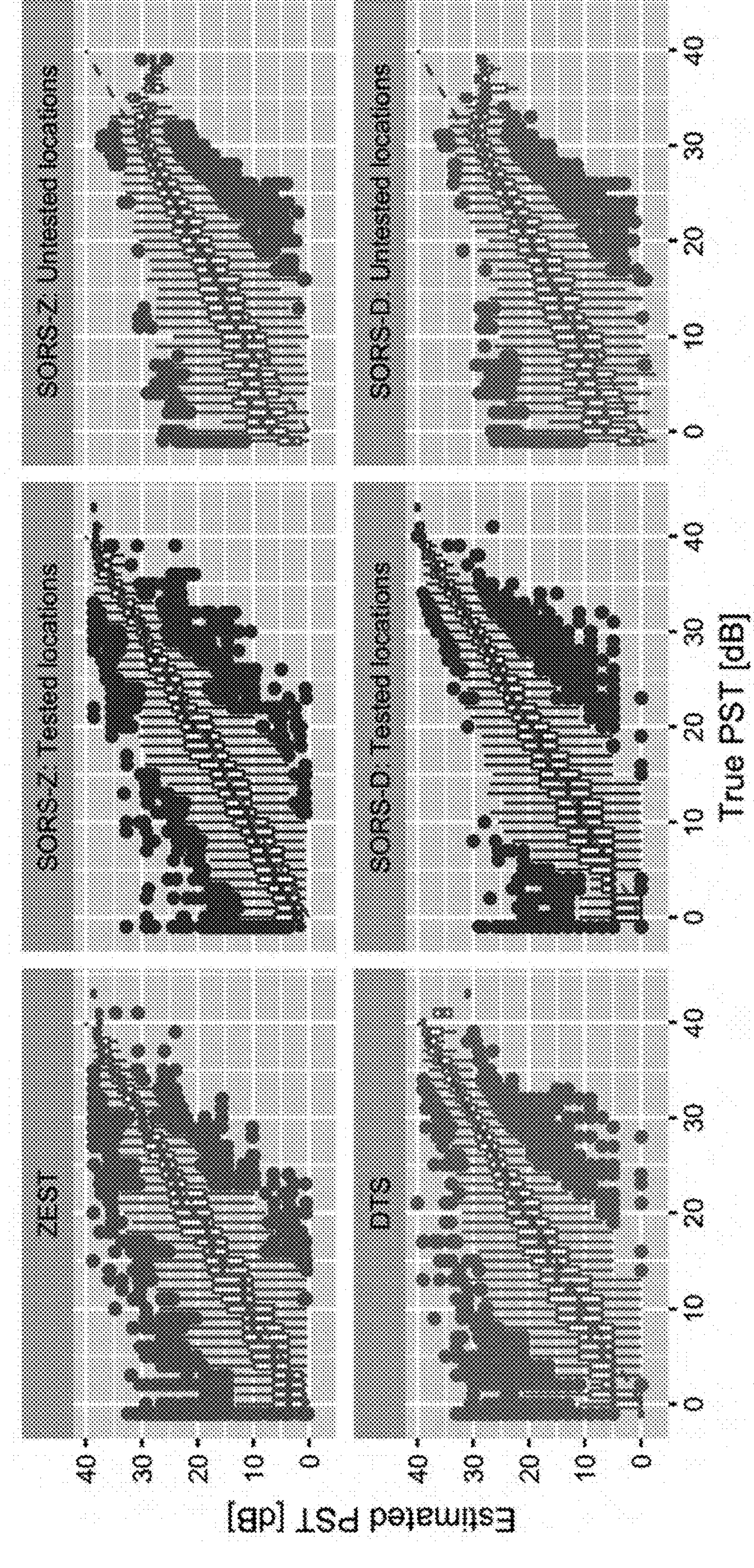
FIG. 8 shows estimated perceived sensitivity threshold versus true perceived sensitivity threshold for SORS, ZEST and DTS. Estimation bias of SORS techniques in tested and untested locations are shown separately. SORS-D and SORS-Z tested 36 locations.

In FIG. 8, we illustrate the estimation bias of the SORS methods with respect to the true perceived sensitivity threshold values found in visual fields, by comparing the predicted perceived sensitivity thresholds with the corresponding true values. We again present results of SORS at tested and untested locations. ZEST and SORS-Z have similar estimation bias trends for tested locations. At untested locations, SORS-Z over-/under-estimates at low and high perceived sensitivity threshold values, respectively. SORS-D however suffers from less bias than DTS at tested locations, whereas it also over-estimates in the low-value range of perceived sensitivity thresholds when inferring untested locations. In general, the reconstruction procedure that SORS performs for the estimation of non-tested locations results in a smoothed reconstruction, thus avoiding values at both extremes of the dB spectrum.

Figure 9:
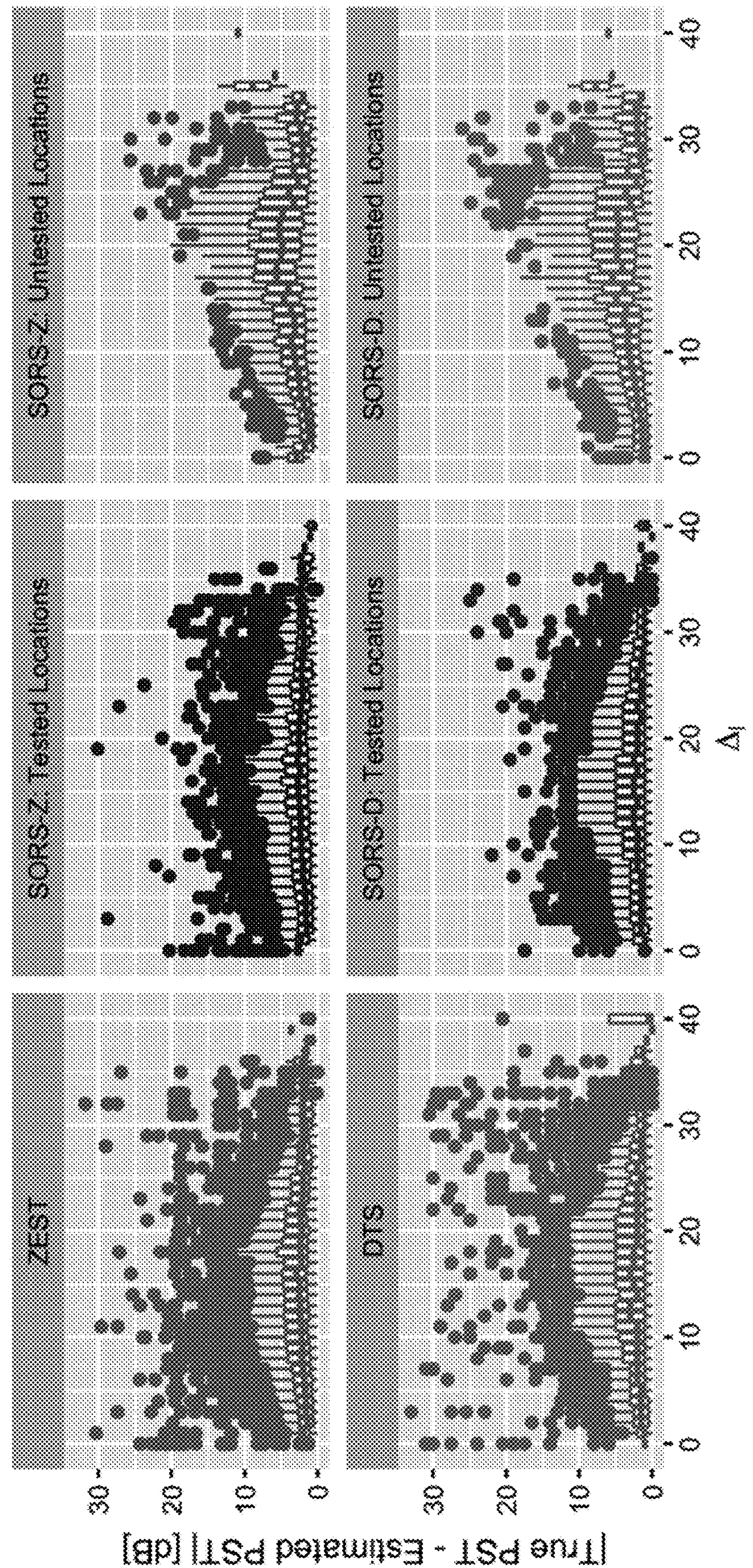
FIG. 9 shows error performance with respect to $\Delta_l$ per location. Absolute errors are presented for ZEST, DTS and SORS-Z and SORS-D. SORS results are separately shown for tested and untested locations. SORS approaches tested 36 locations.

Performance at scotoma borders An important concern with perimetry strategies is their ability to capture scotoma (e. g., regions of isolated impairment). We quantify these regions by computing $\Delta_l = \max_{l_n \in N_l} |t_l - t_{l_n}|$ where $t_l$ is the true perceived sensitivity threshold value at a location l and $t_{l_n}$ is the true perceived sensitivity threshold of location $l_n \in N_l$, $N_l$ being the set of 8-neighbors of location l. FIG. 9 depicts the absolute errors, i. e., $|\hat{t}_l - t_l|$, where $\hat{t}_l$ is the estimated perceived sensitivity threshold value, with respect to $\Delta_l$.

Error box plots for tested and untested locations are given separately for SORS-D and SORS-Z. For the error performances on tested locations, SORS-D and SORS-Z show very similar performances with that of ZEST and DTS, while having slightly fewer outliers. For error performances on untested locations, SORS-D and SORS-Z have low median errors in the low and high value range of $\Delta_l$, while they have increased errors in mid-range scotoma values ($10 \le \Delta_l \le 25$). Even though, SORS leads to higher median and standard deviations of the errors on untested locations, the majority of errors occur within a reasonable range (i. e., less than 8 dB). Moreover, even for untested locations, both SORS methods lead to less outliers than DTS and ZEST.

Figure 10:
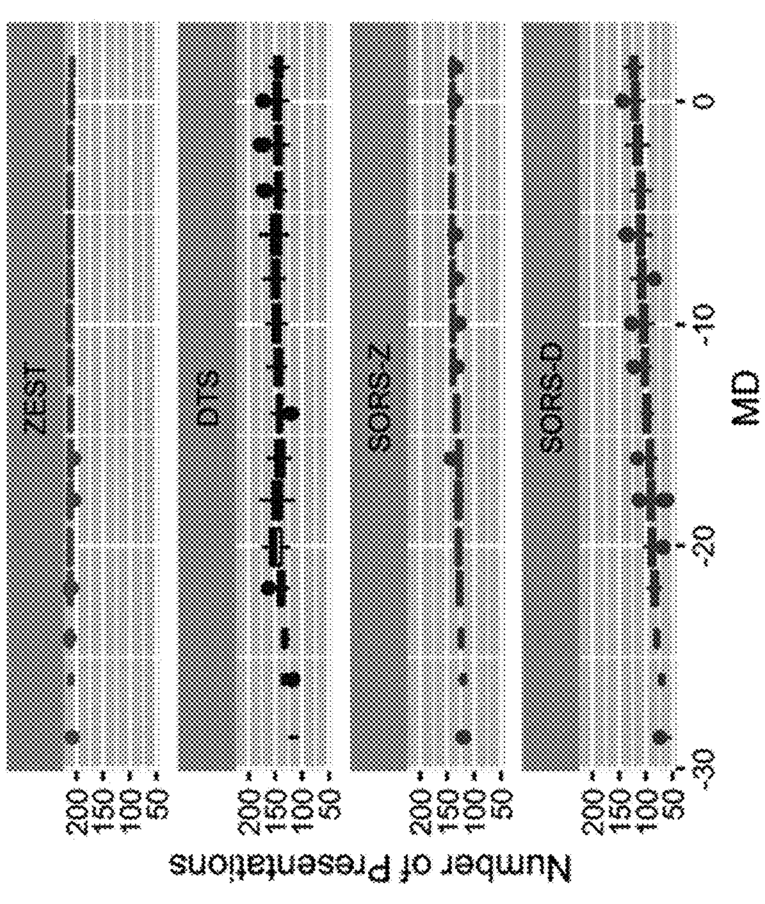
FIG. 10 shows performance dependency of perimetry strategies on mean deviation (MD) in terms of error and speed. We present the dependency of RMSE and number of presentations on MD on the left and right figures respectively. SORS D and SORS-Z tested 36 locations.
Figure 10:
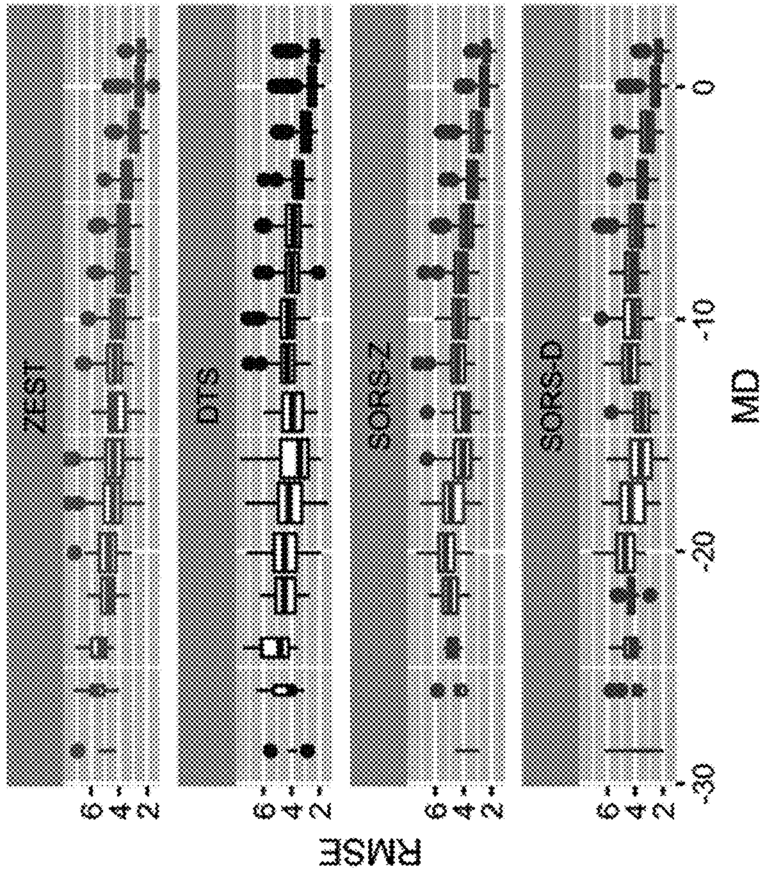

Performance dependency on mean deviation Mean deviation (MD) of a visual field is the average perceived sensitivity threshold deviation from normal reference values collected over a healthy population and is used clinically as an indication of visual impairment. For example, MDs smaller than −2 may signify abnormal eye condition. Accordingly, FIG. 10 shows the relation between MD and RMSE/speed for all tested strategies. In general, the MD-RMSE relation of each method is similar to one another: small RMSE when MD>−10 and no obvious relation for the rest of the MD range. In terms of number of stimuli presentations, ZEST and DTS have no dependency on MD.

Our approaches, especially SORS-D however, appears to depend on MD and surprisingly requires more stimuli for MD>−10. This is due to the fact that within relatively healthy ranges (MD>−10), where SORS-D uses small step sizes in its adaptive staircasing perceived sensitivity threshold estimation method which leads to high precision but slower examinations.

Figure 11:
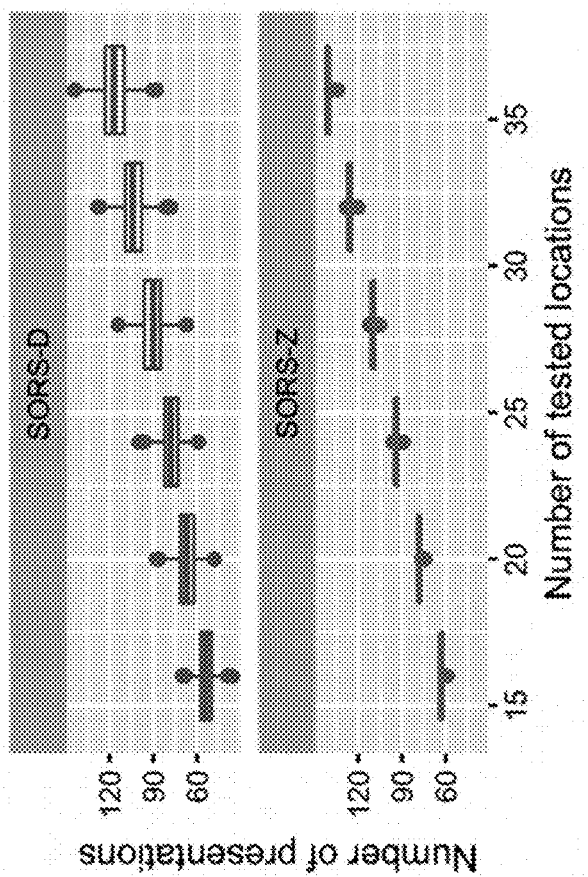
FIG. 11 shows performance dependency of SORS on the number of tested locations for healthy or early glaucomatous visual fields (mean deviation, MD>−6). We present the dependency of RMSE and number of presentations on MD on the left and right figures, respectively. RMSE slightly changes with the increasing number of tested locations. With approximately 20 locations tested, SORS can double the speed without compromising accuracy.
Figure 11:
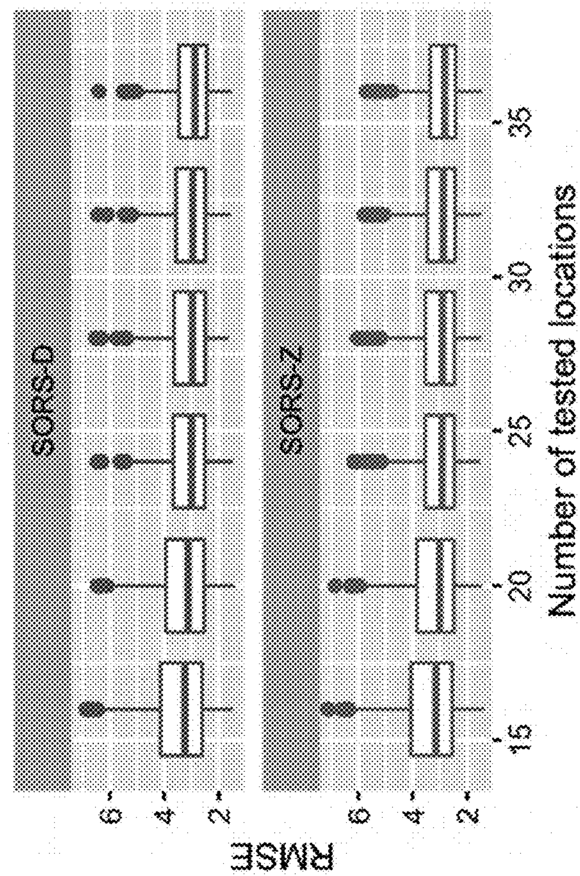

FIG. 11 shows the RMSE and the total number of stimuli presentations with respect to the number of tested locations in SORS-D and SORS-Z for cases of healthy and early glaucomatous visual fields. As can be seen, there is little difference in the average RMSE with respect to number of tested locations. This implies that one can finish SORS earlier for healthier visual fields without compromising accuracy.

Discussion and conclusions We presented a novel Standard Automated Perimetry meta-strategy to quickly acquire visual fields accurately. Our approach leverages the correlations between visual field locations in order to reconstruct the entire visual field from few observed locations. Such a procedure allows our method to be applied at test time in an adaptive way and enables fast convergence to an estimated visual field without having to test all locations. We showed experimentally that SORS speeds up perimetry examination without heavily compromising visual field accuracy and in some cases outperforms state-of-the-art methods outright. This was shown both on healthy and glaucomatous subjects.

While providing better accuracy-speed trade-off, SORS however has some important limitations. SORS is a purely data-driven approach with no parameters to tune except S, the number of visual field locations to be tested. As shown in above, healthier visual fields need fewer number of locations to be tested than glaucomatous visual fields. SORS therefore could be stopped earlier in cases where no further testing is needed. In its current form, SORS does not have an early stopping criterion, therefore it cannot adapt to a given visual field at test time. Another limitation of SORS is its deterministic collections of optimal test locations. As shown in FIG. 5, the optimized sequence of test locations can differ for healthy or glaucomatous subjects, which could confine its performance. An online procedure for selecting locations during the examination time, e. g., selecting location with high uncertainty would circumvent such a limitation. In effect, SORS is population-specific in its approach but not patient-specific. These two main limitations are left as open problems that we will investigate in the future.

Figure 12:
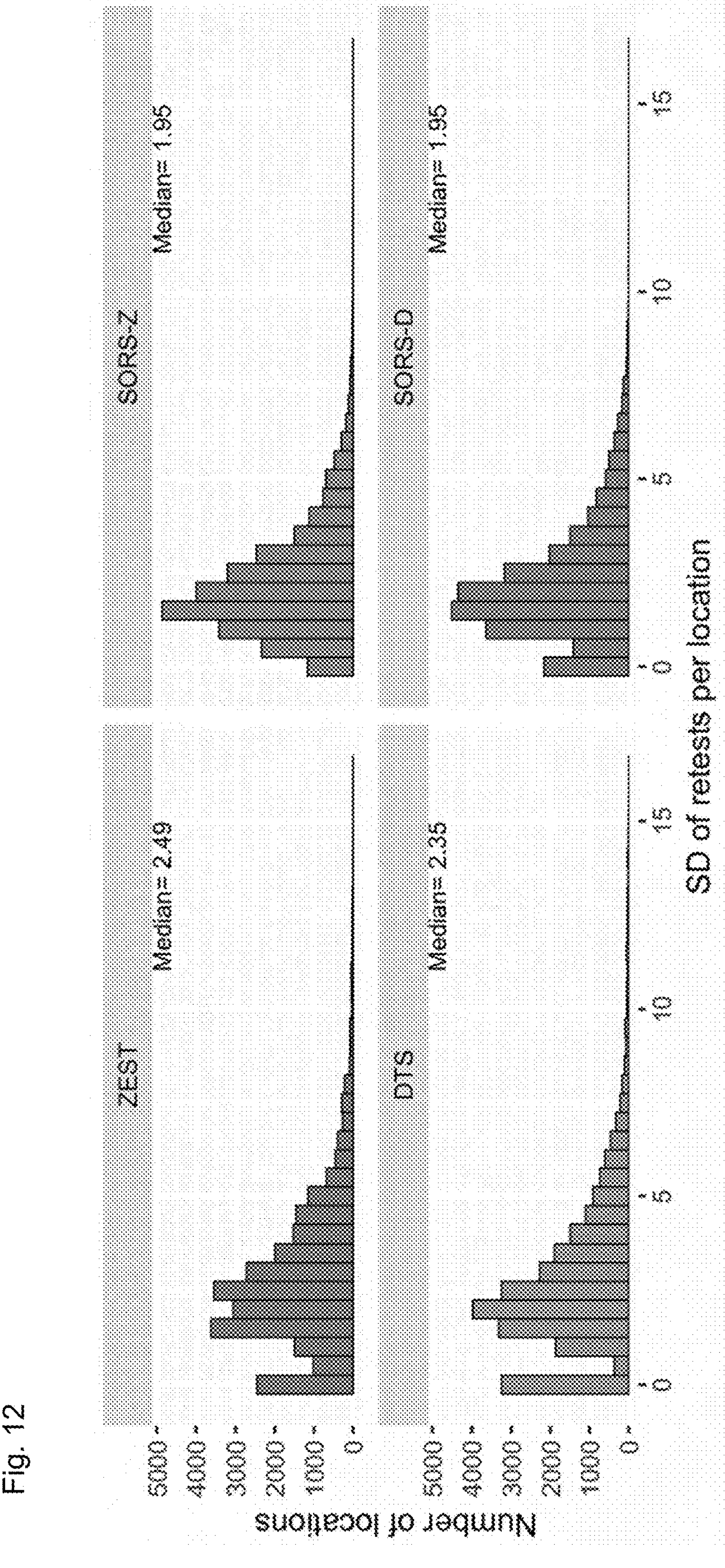
FIG. 12 shows test-retest variability of perimetry strategies. Standard deviations (SDs) of perceived sensitivity threshold estimations of 5 tests per location are presented and the median of each distribution is shown in the top right corner. SORS approaches were tested with 36 locations.

Test-retest variability In order to see how much variability our approach induces if the same subject were to be tested multiple times, we tested 5 times the same visual field with SORS-D and SORS-Z. We present distributions of the standard deviations of the perceived sensitivity threshold estimations for both our approaches as well as for ZEST and DTS in FIG. 12. As can be seen from the median SDs, SORS approaches have less test-retest variability than either ZEST or DTS. This result demonstrates the reproducibility of SORS-acquired visual fields, even with certain locations left untested.

Figure 13:
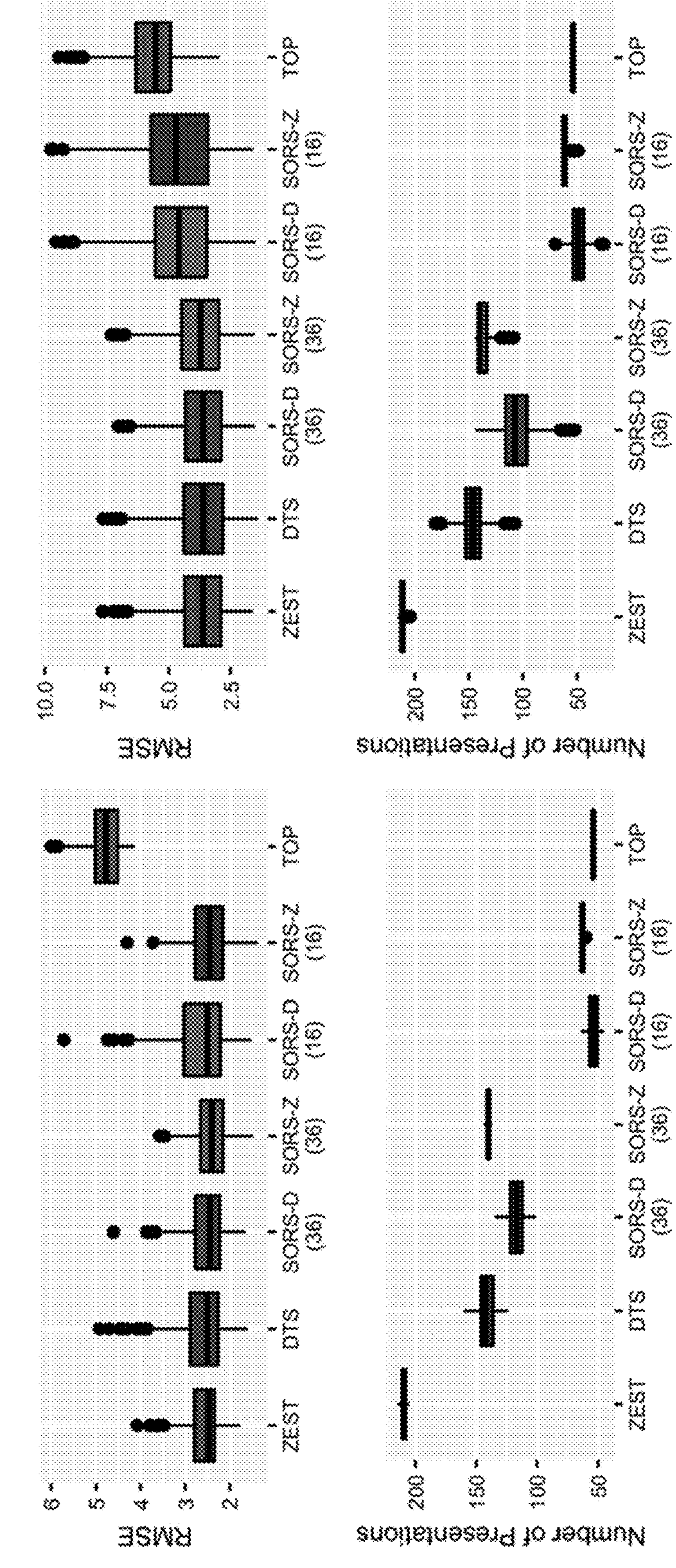
FIG. 13 shows performance comparison of perimetry strategies on different sub-populations. We present SORS performance on healthy (left) and glaucomatous (right) visual fields compared to state-of-the-art methods.

Performance on sub-populations Given that not all visual fields are not of equal health, FIG. 13 (left) and FIG. 13 (right) depict the performance results of each method with respect to different populations, namely healthy and glaucomatous patients. Since glaucomatous samples were abundant in the mixed population set, similar performance were obtained for glaucomatous case as in the mixed population set. In general, using only 16 tested locations, SORS strategies yield more accurate visual fields than DTS and ZEST.

Figure 14:
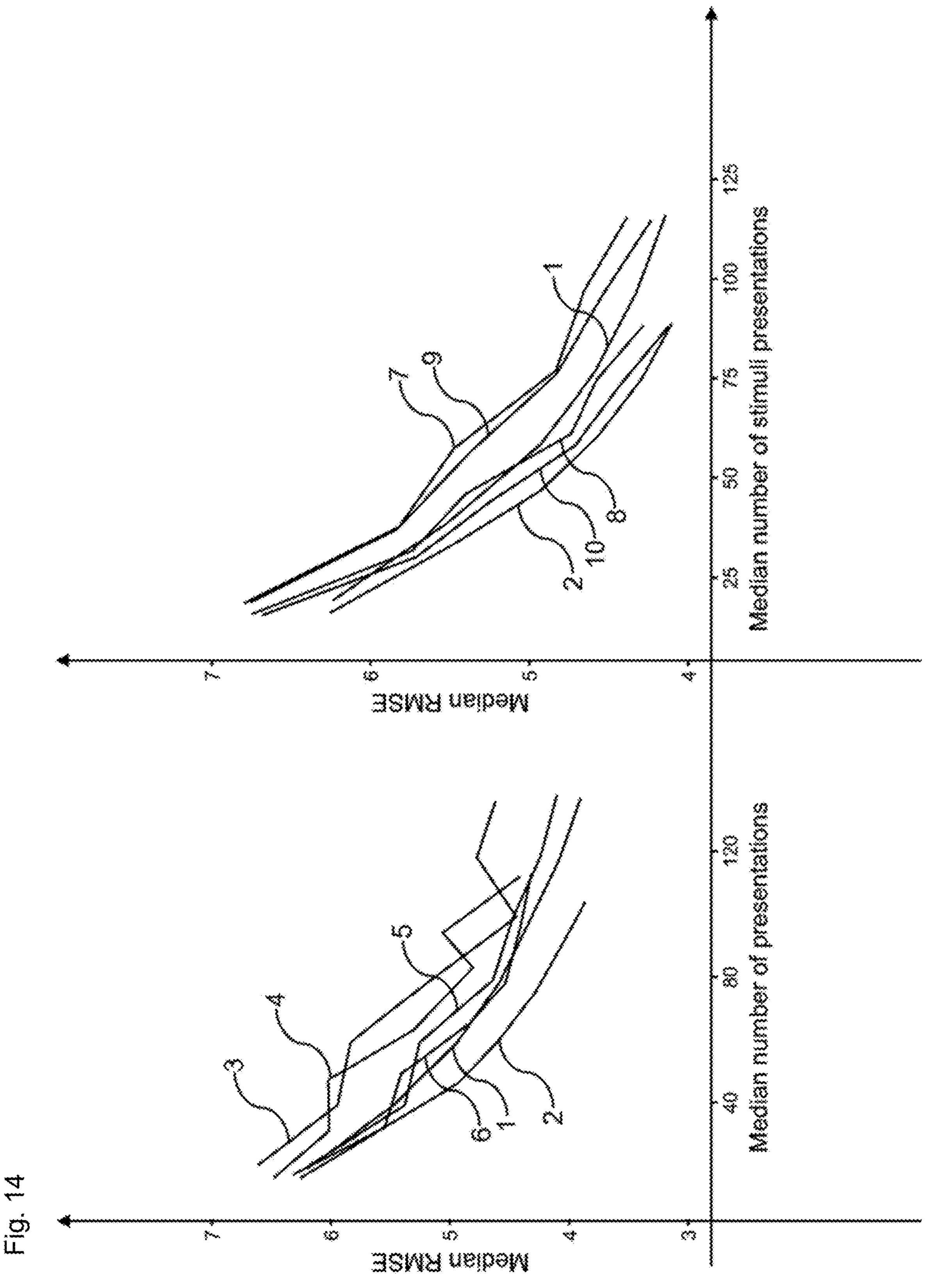
FIG. 14 shows performance comparison between SORS and alternative optimization schemes, namely Reconstruction Strategy (RS) and Optimized Reconstruction Strategy (ORS). We present one version of RS and ORS where there is no intermediate reconstruction step in test time (left) and on the second version where intermediate reconstruction steps were incorporated, called RSv2 and ORSv2 (right).
Figure 15:
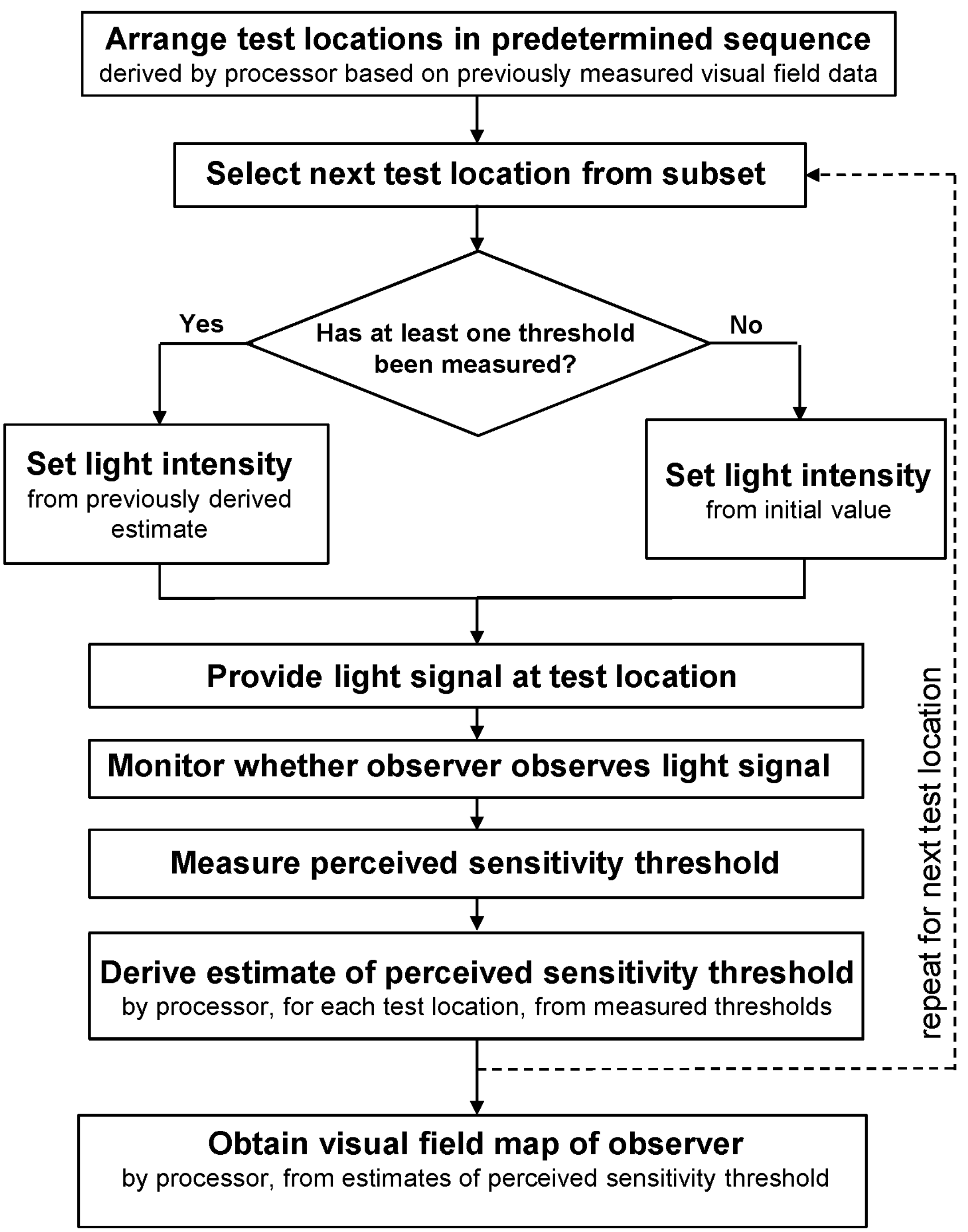
FIG. 15 shows a flowchart illustrating an embodiment of the method according to the present invention.

Optimization scheme To illustrate the advantage of our greedy optimization strategy presented above, we also compare it to two alternatives in FIG. 14. The first, is Reconstruction Strategy (RS) 3, 4, 7, 8, where we randomly select S in order to build a reconstruction dictionary. The second is Optimized Reconstruction Strategy (ORS) 5, 6, 9, 10, where we select in one step a sequence of S locations that minimizes the RMSE by randomly sampling 50 combinations of S locations. Importantly, ORS differs from SORS in that it does not iteratively optimize the location to pick based on the previously selected locations. As seen in FIG. 14 (left), SORS-Z 1 outperforms RS-Z 3 and RS-D 4 in terms of accuracy-speed trade-off. Similarly, SORS-D 2 outperforms RS-D 4 and ORS-D 6. One can easily see performance difference between two versions of reconstruction schemes: an algorithm using adaptive staircasing always outperform its Bayesian perceived sensitivity threshold counterpart. As discussed earlier, this is mainly due to the fact that parameters of Bayesian perceived sensitivity threshold estimation scheme need to be optimized to a specific data set so to perform better than adaptive staircasing.

In the presented RS and ORS in FIG. 14 (left), testing scheme is different than SORS: there is no intermediate reconstruction between testing two consecutive locations as in SORS, but reconstruction takes place once after all S locations are tested. In this regard, SORS may seem to be advantageous in testing time due to its intermediate reconstruction steps. To remove this testing scheme bias, we incorporated intermediate reconstruction steps into RS and ORS, which we call RSv2 7,8 and ORSv2 9,10 and compared them to SORS 1,2, as presented in FIG. 14 (right). Results show that RSv2 7,8 and ORSv2 9,10 still perform worse than their corresponding SORS versions 1,2. This clearly shows that the selection of test locations with associated basis matrices which SORS computes is better optimized than what RS and ORS yield.

| List of reference signs | |
|---|---|
| 1 | SORS-ZEST |
| 2 | SORS-Dynamic |
| 3 | Reconstruction Strategy (RS) - ZEST |
| 4 | Reconstruction Strategy (RS) - Dynamic |
| 5 | Optimized Reconstruction Strategy (ORS) - ZEST |
| 6 | Optimized Reconstruction Strategy (ORS) - Dynamic |
| 7 | Reconstruction Strategy - ZEST v2 (RS-Zv2) |
| 8 | Reconstruction Strategy - Dynamic v2 (RS-Dv2) |
| 9 | Optimized Reconstruction Strategy - ZEST v2 (ORSZv2) |
| 10 | Optimized Reconstruction Strategy - Dynamic v2 (ORSDv2) |
| $\Omega_S$ | Sequence |
| D | Reconstruction matrix |
| $\hat{e}_k$ | Vector of estimates |
| X | Training matrix |
| $Y_{\Omega_S}$ | Measurement matrix |
| $\Omega_{k-1,l}$ | Initial sequence |
| $l_k^*$ | Element |
| $\mu$ | Mean |
| $nv_l$ | Normative value |

We claim:

1. A method for obtaining a visual field map of an observer, wherein a plurality of test locations in front of the observer is provided, wherein the plurality of test locations is arranged in a predetermined sequence which has been derived by at least one processor based on previously measured visual field data, at each test location of a subset of said plurality of test locations a respective perceived sensitivity threshold of the observer is measured, wherein at least one light signal is provided at the respective test location, and wherein it is monitored whether said observer observes said at least one light signal, and wherein for each test location of said plurality of test locations a respective estimate of the perceived sensitivity threshold is derived by at least one processor from the previously measured perceived sensitivity thresholds of said subset of test locations, and wherein in case at least one perceived sensitivity threshold of the test locations of said subset has been measured, said at least one light signal at a respective test location of said subset is provided at a light intensity value which is derived from the previously derived estimate of the perceived sensitivity threshold of said respective test location, and wherein the visual field map of the observer is obtained by at least one processor from the estimates of the perceived sensitivity threshold of said plurality of test locations.

2. The method according to claim 1, wherein the number of test locations in said subset is smaller than the number of test locations in said plurality of test locations.

3. The method according to claim 1, wherein said respective estimate of the perceived sensitivity threshold is derived from the previously measured perceived sensitivity thresholds of said subset of test locations by means of a function defining a relationship between said respective estimate and said previously measured perceived sensitivity thresholds.

4. The method according to claim 3, wherein said function is a linear function or a non-linear function.

5. The method according to claim 1, wherein a sequence ($\Omega_S$) comprising the test locations of said subset is provided, and wherein the respective perceived sensitivity thresholds of the test locations of said subset are measured in the order of said sequence ($\Omega_S$).

6. The method according to claim 4, wherein a set of reconstruction matrices (D) is provided consisting of matrices $$D_k^{l_k^*}$$

each matrix $$D_k^{l_k^*}$$

comprising coefficients of said linear function, and wherein a respective vector ($\hat{e}_k$) of estimates of the perceived sensitivity threshold is derived from the previously measured perceived sensitivity thresholds of said subset of test locations by means of the formula $$\hat{e}_k = D_k^{l_k^*} y_{\Omega_k^*},$$

wherein $$D_k^{l_k^*}$$

is a basis matrix of size M×k, wherein k is the number of test locations of said subset at which perceived sensitivity thresholds have been previously measured, and wherein $$Y_{\Omega_k^*}$$

is a measurement vector comprising said previously measured perceived sensitivity thresholds of said subset of test locations.

7. The method according to claim 6, wherein a final reconstruction matrix Ď, wherein Ď corresponds to $$D_S^{l_S^*},$$

and said sequence ($\Omega_S$) are determined by means of a training matrix (X), wherein each respective column of said training matrix (X) comprises a plurality of previously measured perceived sensitivity thresholds of a respective observer, wherein each perceived sensitivity threshold has been measured at a respective test location, and wherein a measurement matrix ($Y_{\Omega_S}$), is provided, wherein the measurement matrix ($Y_{\Omega_S}$) is a sub-matrix of said training matrix (X), wherein the rows of the measurement matrix ($Y_{\Omega_S}$) are identical to or a noisy version of the rows of the training matrix (X) indexed by said sequence ($\Omega_S$), and wherein said final reconstruction matrix Ď and said sequence ($\Omega_S$) are determined such that an error $$\|X - \check{D} Y_{\Omega_S}\|_2^2$$

is minimized.

8. The method according to claim 7, wherein said reconstruction matrix Ď and said sequence ($\Omega_S$) are determined by providing an initial sequence ($\Omega_{k-1,l}$) and an initial measurement matrix ($Y_{\Omega k-1,l}$), wherein the initial measurement matrix ($Y_{\Omega_{k-1,l}}$) is a sub-matrix of said training matrix (X), wherein the rows of the initial measurement matrix ($Y_{\Omega_{k-1,l}}$), are identical to or a noisy version of the rows of the training matrix (X) indexed by said initial sequence ($\Omega_{k-1,l}$), and wherein an element $$(l_k^*)$$

is added to said initial sequence ($\Omega_{k-1,l}$), wherein said element $$(l_k^*)$$

is the argument of the minimum of the expression $$\|X - D^l Y_{\Omega_{k-1,l}}\|_2^2,$$

wherein $$D_k^l$$

is a basis matrix defined by $$D_k^l = XY_{\Omega_{k-1,l}}^T \left(Y_{\Omega_{k-1,l}} Y_{\Omega_{k-1,l}}^T\right)^{-1},$$

wherein $$Y_{\Omega_{k-1,l}}^T$$

designates the transposed initial measurement matrix, and wherein $$\left(Y_{\Omega_{k-1,l}}^T Y_{\Omega_{k-1,l}}\right)^{-1}$$

designates the inverse matrix of the matrix product $$Y_{\Omega_{k-1,l}} Y_{\Omega_{k-1,l}}^T.$$

9. The method according to claim 1, wherein said at least one light signal comprises a first light signal and a subsequent second light signal, wherein the method comprises monitoring whether said observer has observed said first light signal and monitoring whether said observer has observed said second light signal, wherein in case the observer has not observed the first light signal, the light intensity value of the second light signal is increased compared to the light intensity value of the first light signal, and wherein in case the observer has observed the first light signal, the light intensity value of the second light signal is decreased compared to the light intensity value of the first light signal.

10. The method according to claim 9, wherein in case said observer has not observed said first light signal and said observer has observed said second light signal or in case said observer has observed said first light signal and said observer has not observed said second light signal, said perceived sensitivity threshold of the respective test location is assigned said light intensity value of said second light signal.

11. The method according to claim 9, wherein said light intensity value of the second light signal is increased or decreased by a first difference, and wherein said at least one light signal comprises a third light signal provided subsequently to the second light signal, wherein in case the observer has not observed the second light signal, the light intensity value of the third light signal is increased by a second difference compared to the light intensity value of the second light signal, and wherein in case the observer has observed the second light signal, the light intensity value of the third light signal is decreased by said second difference compared to the light intensity value of the second light signal, wherein said second difference equals the first difference multiplied by a factor, wherein particularly said factor is 2.

12. The method according to claim 11, wherein in case said observer has not observed said second light signal and said observer has observed said third light signal, or in case said observer has observed said second light signal and said observer has not observed said third light signal, said perceived sensitivity threshold of the respective test location is assigned said light intensity value of said third light signal.

13. The method according to claim 9, wherein a respective initial probability mass function $$\left(PMF_{k+1}^{l*}\right)$$

defined by the formula $$PMF_{k+1}^{l*} = G\left(\mu, \sigma_l^2\right) + \alpha G(0, 1) + \epsilon_l,$$

is provided for each test location of said subset of test locations, wherein $$G\left(\mu, \sigma_l^2\right)$$

is a first Gaussian function, wherein μ designates a mean of said first Gaussian function, and wherein $$\sigma_l^2$$

designates a standard deviation of said first Gaussian function, and wherein G(0,1) is a second Gaussian function having a mean of 0 and a standard deviation of 1, and wherein α is a weight parameter between 0 and 1, and wherein $\epsilon_l$ is a constant, wherein particularly before measuring said at least one perceived sensitivity threshold, said mean (μ) of said first Gaussian function is assigned an age-matched normative value ($nv_1$) of the perceived sensitivity threshold at the respective test location, and wherein after obtaining at least one perceived sensitivity threshold, said mean (μ) of said first Gaussian function is assigned the previously derived estimate of the perceived sensitivity threshold of said respective test location, and wherein said first light signal is provided at a light intensity value which is equal to said mean (μ) of said first Gaussian function, and wherein after monitoring whether the observer has observed said first light signal, an updated probability mass function is derived by multiplying the probability mass function by a likelihood function, particularly having a sigmoidal shape, wherein said likelihood function is monotonously increasing in case the observer has observed said light signal, and wherein said likelihood function is monotonously decreasing in case the observer has not observed said light signal, and wherein said second light signal is provided at a light intensity value which is equal to the mean of said updated probability mass function.

14. The method according to claim 13, wherein in case a standard deviation of said updated probability mass function is larger than or equal to a first stop value, a further light signal is provided, particularly at an intensity value equal to the mean of the updated probability mass function, wherein the method comprises monitoring whether said observer has observed said further light signal, and wherein a further updated probability mass function is generated by multiplying the previous probability mass function with a likelihood function, wherein said likelihood function is monotonously increasing in case the observer has observed said further light signal, and wherein said likelihood function is monotonously decreasing in case the observer has not observed said further light signal, and wherein in case said standard deviation of said updated probability mass function is smaller than said first stop value, said sensitivity estimate of the respective test location is assigned the value of the mean of said updated probability mass function.

15. The method according to claim 9, wherein in case the total number of light signals provided at the respective test location is smaller than or equal to a second stop value, a further light signal is provided at said respective test location, and the method comprises monitoring whether said observer has observed said further light signal.

16. A method for obtaining a visual field map of an observer, wherein a plurality of test locations in front of the observer is provided, wherein the plurality of test locations is arranged in a predetermined sequence which is derived by at least one processor based on previously measured visual field data, at each test location of a subset of said plurality of test locations a respective perceived sensitivity threshold of the observer is measured, wherein at least one light signal is provided at the respective test location, and wherein it is monitored whether said observer observes said at least one light signal, and wherein for each test location of said plurality of test locations a respective estimate of the perceived sensitivity threshold is derived by at least one processor from the previously measured perceived sensitivity thresholds of said subset of test locations, and wherein in case at least one perceived sensitivity threshold of the test locations of said subset has been measured, said at least one light signal at a respective test location of said subset is provided at a light intensity value which is derived from the previously derived estimate of the perceived sensitivity threshold of said respective test location, and wherein the visual field map of the observer is obtained by at least one processor from the estimates of the perceived sensitivity threshold of said plurality of test locations.

* * * * *